United States Patent
Poupko et al.

(10) Patent No.: US 8,211,031 B2
(45) Date of Patent: Jul. 3, 2012

(54) NON-INVASIVE INTRACRANIAL MONITOR

(75) Inventors: Ben Zion Poupko, Ness Ziona (IL); Yosef Reichman, Kfar-Saba (IL); Alon Rappaport, Tel-Aviv (IL); Shlomi Ben-Ari, Binyamina (IL)

(73) Assignee: Orsan Medical Technologies Ltd. (IL)

( * ) Notice: Subject to any disclaimer, the term of this patent is extended or adjusted under 35 U.S.C. 154(b) by 1530 days.

(21) Appl. No.: 11/610,553

(22) Filed: Dec. 14, 2006

(65) Prior Publication Data

US 2007/0287899 A1    Dec. 13, 2007

Related U.S. Application Data

(63) Continuation-in-part of application No. PCT/IB2006/050174, filed on Jan. 17, 2006, which is a continuation-in-part of application No. PCT/IL2005/000631, filed on Jun. 15, 2005, and a continuation-in-part of application No. PCT/IL2005/000632, filed on Jun. 15, 2005, said application No. PCT/IL2005/000631 is a continuation-in-part of application No. 10/893,570, filed on Jul. 15, 2004, now Pat. No. 7,998,080, said application No. PCT/IL2005/000632 is a continuation-in-part of application No. 10/893,570, which is a continuation-in-part of application No. PCT/IL03/00042, filed on Jan. 15, 2003.

(60) Provisional application No. 60/348,278, filed on Jan. 15, 2002.

(51) Int. Cl.
*A61B 5/02* (2006.01)
*A61B 5/04* (2006.01)

(52) U.S. Cl. ......................... 600/506; 600/383

(58) Field of Classification Search ............... 600/383, 600/506, 553, 545, 547
See application file for complete search history.

(56) References Cited

U.S. PATENT DOCUMENTS

| 3,871,359 A * | 3/1975 | Pacela ........................... 600/547 |
|---|---|---|
| 4,308,873 A | 1/1982 | Maynard |
| 4,649,932 A | 3/1987 | Smith |
| 4,984,567 A | 1/1991 | Kageyama et al. |
| 5,040,540 A | 8/1991 | Sackner |
| 5,068,619 A | 11/1991 | Nakano et al. |
| 5,265,615 A | 11/1993 | Frank et al. |

(Continued)

FOREIGN PATENT DOCUMENTS

DE    10061189    6/2002

(Continued)

OTHER PUBLICATIONS

Letter in Reponse Dated Dec. 7, 2010 to Telephone Conference With Examiner of Dec. 7, 2010 From the International Bureau of WIPO Re. Application No. PCT/IB2009/054392.

(Continued)

*Primary Examiner* — Patricia Mallari
*Assistant Examiner* — Christian Jang
(74) *Attorney, Agent, or Firm* — Finnegan, Henderson, Farabow, Garrett & Dunner, L.L.P.

(57) ABSTRACT

A method of estimating at least one intracranial hemodynamic parameter in a subject, the method comprising:
 a) obtaining data of changes in electrical impedance across the subject's head as a function of time;
 b) analyzing the data; and
 c) estimating one or more of intracranial pressure, cerebral blood volume, and a factor related to at least one of cerebral perfusion pressure and a mean transit time through cerebral capillaries.

18 Claims, 7 Drawing Sheets

U.S. PATENT DOCUMENTS

Figure 1:
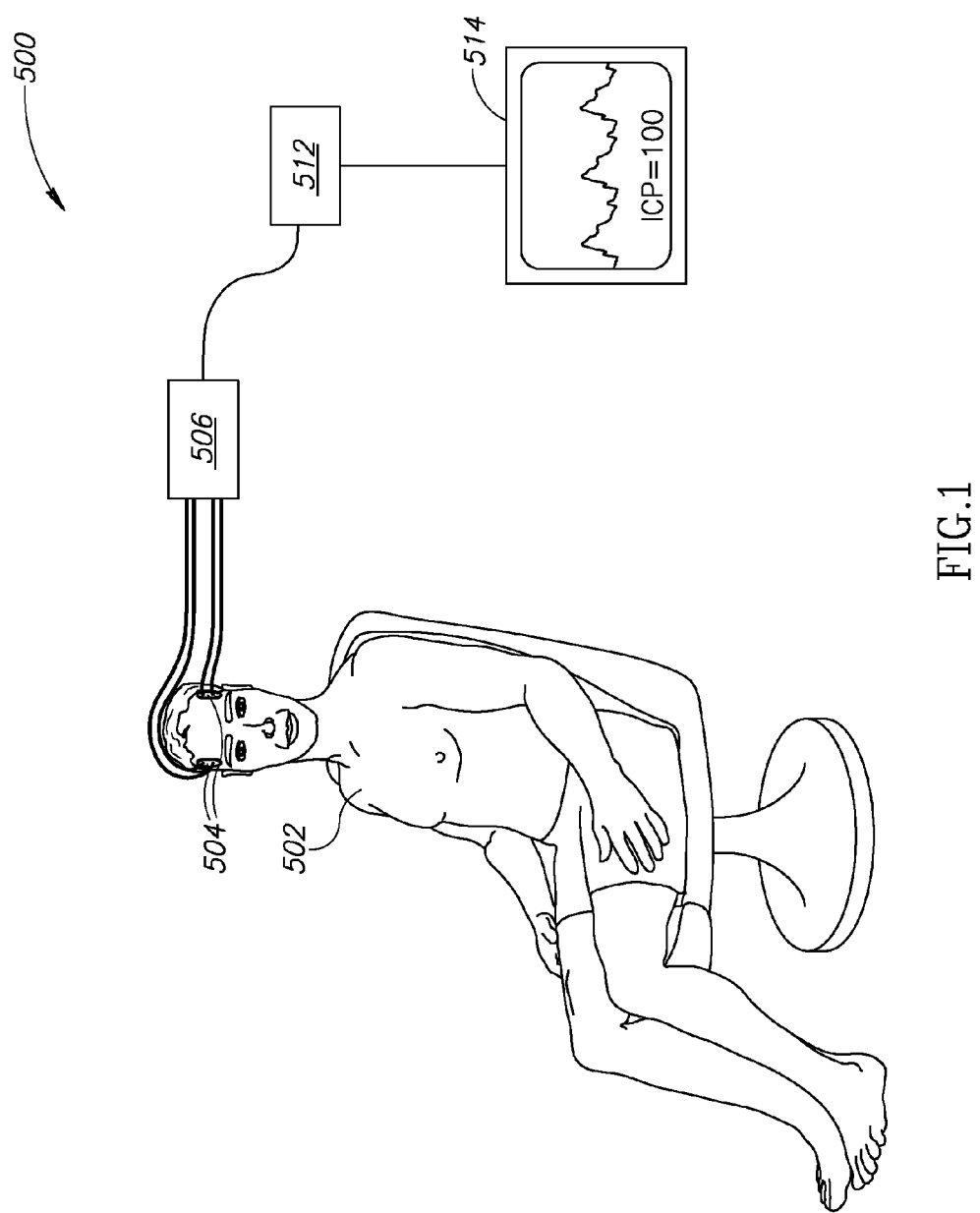

| | | | |
|---|---|---|---|
| 5,282,840 A | 2/1994 | Hudrlik | |
| 5,353,802 A | 10/1994 | Ollmar et al. | |
| 5,396,893 A | 3/1995 | Oberg et al. | |
| 5,584,297 A * | 12/1996 | Bodo et al. | 600/483 |
| 5,694,939 A | 12/1997 | Cowings | |
| 5,746,214 A | 5/1998 | Brown et al. | |
| 5,749,369 A | 5/1998 | Rabinovich et al. | |
| 5,788,643 A | 8/1998 | Feldman | |
| 6,081,743 A * | 6/2000 | Carter et al. | 600/544 |
| 6,091,977 A | 7/2000 | Tarjan et al. | |
| 6,117,089 A | 9/2000 | Sinha | |
| 6,169,914 B1 | 1/2001 | Hovland et al. | |
| 6,223,069 B1 | 4/2001 | Pfeiffer et al. | |
| 6,245,027 B1 | 6/2001 | Alperin | |
| 6,413,223 B1 | 7/2002 | Yang et al. | |
| 6,491,647 B1 | 12/2002 | Bridger et al. | |
| 6,773,407 B2 | 8/2004 | Yost et al. | |
| 6,819,950 B2 | 11/2004 | Mills | |
| 6,832,113 B2 | 12/2004 | Belalcazar | |
| 6,875,176 B2 | 4/2005 | Mourad et al. | |
| 6,976,963 B2 | 12/2005 | Clift | |
| 6,996,428 B2 | 2/2006 | Kislov et al. | |
| 7,041,063 B2 | 5/2006 | Abreu | |
| 7,998,080 B2 * | 8/2011 | Ben-Ari et al. | 600/506 |
| 2004/0010185 A1 | 1/2004 | Kimball et al. | |
| 2004/0030258 A1 | 2/2004 | Williams et al. | |
| 2004/0034294 A1 | 2/2004 | Kimball et al. | |
| 2004/0049105 A1 | 3/2004 | Crutchfield et al. | |
| 2005/0054939 A1 | 3/2005 | Ben-Ari et al. | |
| 2006/0094964 A1 | 5/2006 | Ragauskas et al. | |
| 2006/0122523 A1 | 6/2006 | Bonmassar et al. | |
| 2006/0200033 A1 | 9/2006 | Keren et al. | |
| 2008/0004904 A1 | 1/2008 | Tran | |
| 2008/0021332 A1 | 1/2008 | Brainard, III | |
| 2008/0200787 A1 | 8/2008 | Shapira et al. | |
| 2008/0275352 A1 | 11/2008 | Shapira et al. | |
| 2009/0227881 A1 | 9/2009 | Reichman et al. | |

FOREIGN PATENT DOCUMENTS

| | | |
|---|---|---|
| EP | 0314088 | 5/1989 |
| EP | 1057498 | 12/2000 |
| GB | 1538695 | 1/1979 |
| JP | 01-113645 | 5/1989 |
| JP | 03-118038 | 5/1991 |
| JP | 06-078888 | 3/1994 |
| JP | 2000-325324 | 11/2000 |
| JP | 2001-104274 | 4/2001 |
| JP | 2002-010986 | 1/2002 |
| JP | 2005-500116 | 1/2005 |
| RU | 2141249 | 11/1999 |
| WO | WO 96/16692 | 6/1996 |
| WO | WO 02/071923 | 9/2002 |
| WO | WO 02/087410 | 11/2002 |
| WO | WO 03/017834 | 3/2003 |
| WO | WO 03/059164 | 7/2003 |
| WO | WO 2006/006143 | 1/2006 |
| WO | WO 2006/011128 | 2/2006 |
| WO | WO 2006/087696 | 8/2006 |
| WO | WO 2006/134501 | 12/2006 |
| WO | WO 2008/072223 | 6/2008 |
| WO | WO 2006/087696 | 8/2008 |
| WO | WO 2010/041204 | 4/2010 |
| WO | WO 2010/041205 | 4/2010 |
| WO | WO 2010/041206 | 4/2010 |

OTHER PUBLICATIONS

Letter in Reponse Dated Dec. 7, 2010 to Telephone Conference With Examiner of Dec. 7, 2010 From the International Bureau of WIPO Re. Application No. PCT/IB2009/054394.

Translation of Notificiation of Reasons for Rejection Dated Dec. 14, 2010 From the Japanese Patent Office Re. Application No. 2007-520969.

Czosnyka "Cerebral Perfusion in Head-Injured Patients: A Nonivasive Assessment Using Transcranial Doppler Ultrasonography", Journal of Neurosurgery, 88: 802-808, 1998.

Ragauskas et al. "Implement of Non-Invasive Brain Physiological Moniitoring Concepts", Medical Engineering & Physics 25: 667-678, 2003.

Traczewski et al. "The Role of Computerized Rheoencephalography in the Assessment of Normal Pressure Hydrocephalus",Journal of Neutrotrauma, 22 (7): 836-843, 2005.

Wintermark et al. "Comparatibe Overview of Brain Perfusion Imaging Techniques", Stroke, vol. 36e, p. 83-99, 2005.

Braunfels et al., "A Randomized, Controlled Trial of the Efficacy of Closed Chest Compressions in Ambulances", Preshop Emrge Care, 1(3): 128-131, 1997.

Grönlund et al., "High Frequency Variability of Trancephalic Electrical Impedance. A New Parameter for Monitoring of Neonatal Cerebral Circulation?", Proceedings of the Annual International Conference of the Engineering in Medicine and Biology Society, 6: 2513-2515.

Seipel et al., "Rheoencephalographic and Other Studies of Betahistine in Humans: I. The Cerebral and Peripheral Circulatory Effects of Single Doses in Normal Subjects", The Journal of Clinical Pharmacology, 15: 144-154, 1975.

Webster, "Measurement of Flow and Volume of Blood", Medical Instrumentation: Appliccation and Design: 332-371, 1997.

International Preliminary Report on Patentability Dated Dec. 21, 2010 From the International Preliminary Examining Authority Re. Application No. PCT/IB2009/054392.

International Preliminary Report on Patentability Dated Dec. 27, 2010 From the International Preliminary Examining Authority Re.: Application No. PCT/IB2009/054394.

Communication Relating to the Results of the Partial International Search Dated Dec. 28, 2009 From the International Searching Authority Re.: Application No. PCT/IB2009/054392.

Communication Relating to the Search of the Partial International Search Dated Dec. 29, 2009 From the International Searching Authority Re.: Application No. PCT/IB2009/054388.

International Search Report and the Written Opinion Dated Dec. 23, 2009 From the International Searching Authority Re.: Application No. PCT/IB2009/054394.

Official Action Dated Nov. 27, 2009 From the US Patent and Trademark Office Re.: U.S. Appl. No. 10/893,570.

Abboud et al. "Left-Right Asymmetry of Visual Evoked Potentials in Brain-Damaged Patients: A Mathematical Model and Experimental Results", Annals of Biomedical Engineering, XP000578781, 24(1): 75-86, Jan. 1, 1996. Abstract, Fig. 1.

Response Dated Jan. 12, 2011 to Telephone Conference With Examiner of Jan. 12, 2011 From the International Bureau of WIPO Re. Application No. PCT/IB2009/054388.

Bonmassar et al. "The Spape of Electrical Impedance Spectroscopy (EIS) Is Altered in Stroke Patients", Proceedings of the 26th Annual International Conference of the IEEE EMBS, San Francisco, CA, USA, Sep. 1-5, 2005, p. 3443-3446, 2005.

Grönlund et al. "High Frequency Variability of Transcephalic Electrical Impedance—A New Parameter for Monitoring of Neonatal Cerebral Circulation", IEEE, p.2513-2515.

Moshkalenko et al. "Slow Rhythmic Oscillations With the Human Cranium: Phenomenology, Origin, and Informational Significance", Human Physiology, 27(2): 171-178, 2001. Translated From Fiziologiya Cheloveka, 27(2): 47-55, 2001.

Ragauskas et al. "Implementation of Non-Invasive Brain Physiological Monitoring Concepts", Medical Engineering & Physics, 25: 667-678, 2003.

Weindling et al. "Effect of Electrode Size on the contributions of Intracranial and Extracranial Blood Flow to the Cerebral Electrical Impedance Plethysmogram", Medical & Biological Engineering & Computing, 20: 545-549, Sep. 1982.

International Preliminary Report on Patentability Dated Jan. 21, 2011 From the International Preliminary Examining Authority Re. Application No. PCT/IB2009/054388.

Response Dated Jan. 20, 2011 to Official Action of Nov. 5, 2010 From the US Patent and Trademark Office Re.: U.S. Appl. No. 10/893,570.

Bodo, Michael, Rheoencephalographic Changed Suring Increased Intracranial Pressure. Pharamcology of Cerebral Ischemia, Amsterdam, 1986, pp. 265-269, 5 pages.

Costeloe et al. "A Comparison Between Electrical Impedance and Strain Gauge Plethysmography for the Study of Cerebral Blood Flow in the Newborn", Pediatric Research, 18(3): 290-295, Mar. 1984.

Hua et al. "Using Compound Electrodes in Electrical impedance Tomography", IEEE Transactions on Biomedical Engineering, 40(1): 29-34, Jan. 1993.

Weindling et al. "Cerebral Haemodynamics in Newborn Babies Studied by Electrical Impedance", Acta Paediatrica Scandinavica Supplement. 311: 14-19, 1983.

Official Action Dated Dec. 19, 2011 From the US Patent and Trademark Office Re. U.S. Appl. No. 11/572,157.

Restriction Official Action Dated Jan. 6, 2012 From the US Patent and Trademark Office Re. U.S. Appl. No. 11/921,937.

Translation of Notification of Reasons for Rejection Dated Mar. 22, 2011 From the Japanese Patent Office Re. Application No. 2007-520968.

Communication Pursuant to Article 94(3) EPC Dated Apr. 3, 2009 From the European Patent Office Re.: Application No. 05750856.6.

Communication Pursuant to Article 94(3) EPC Dated Feb. 24, 2010 From the European Patent Office Re.: Application No. 07827394.3.

Communication Pursuant to Article 94(3) EPC Dated Mar. 29, 2010 From the European Patent Office Re.: Application No. 05750856.6.

International Preliminary Report on Patentability Dated Jan. 3, 2008 From the International Bureau of WIPO Re.: Application No. PCT/IB2006/050174.

International Preliminary Report on Patentability Dated Nov. 15, 2006 From the International Preliminary Examining Authority Re.: Application No. PCT/IL2005/000631.

International Preliminary Report on Patentability Dated May 23, 2007 From the International Preliminary Examining Authority Re.: Application No. PCT/IL05/00632.

International Preliminary Report on Patentability Dated Mar. 26, 2009 From the International Preliminary Examining Authority Re.: Application No. PCT/IL2007/001421.

International Search Report Dated Dec. 5, 2005 From the International Searching Authority Re.: Application No. PCT/IL05/00632.

International Search Report Dated Oct. 14, 2003 From the International Searching Authority Re.: Application No. PCT/IL03/00042.

International Search Report Dated Oct. 20, 2005 From the International Searching Authority Re.: Application No. PCT/IL2005/000631.

International Search Report Dated May 21, 2008 From the International Searching Authority Re.: Application No. PCT/IL2007/001421.

International Search Report Dated Jun. 23, 2006 From the International Searching Authority Re.: Application No. PCT/IB2006/050174.

Office Action Dated Sep. 5, 2008 From the Patent Office of the People's Republic of China Re.: Application No. 200580031088.2 and Its Translation Into English.

Office Action Dated May 23, 2008 From the Patent Office of the People's Republic of China Re.: Application No. 100580031089.7.

Official Action Dated Mar. 18, 2008 From the US Patent and Trademark Office Re.: U.S. Appl. No. 10/893,570.

Official Action Dated Sep. 19, 2008 From the US Patent and Trademark Office Re.: U.S. Appl. No. 10/893,570.

Rejection Decision Dated Feb. 12, 2010 From the State Intellectual Property Office of the People's Republic of China Re.: Application No. 200580031089.7 and Its Translation Into English.

Response Dated Mar. 1, 2010 to Official Action of Nov. 27, 2009 From the US Patent and Trademark Office Re.: U.S. Appl. No. 10/893,570.

Supplementary European Search Report Dated Jan. 28, 2010 From the European Patent Office Re.: Application No. 05752203.9.

Written Opinion Dated Dec. 5, 2005 From the International Searching Authority Re.: Application No. PCT/IL05/000632.

Written Opinion Dated Oct. 20, 2005 From the International Searching Authority Re.: Application No. PCT/IL2005/000631.

Written Opinion Dated May 21, 2008 From the International Searching Authority Re.: Application No. PCT/IL2007/001421.

Written Opinion Dated Jun. 23, 2006 From the International Searching Authority Re.: Application No. PCT/IB2006/050174.

Barbosa-Silva et al. "Bioelectrical Impedance Analysis: Population Reference Values for Phase Angle by Age and Sex", The American Journal of Clinical Nutrition, 82: 49-52, 2005.

González et al. "A Theoretical Study on Magnetic Induction Frequency Dependence of Phase Shift in Oedema and Haematoma", Physiological Measurement, 27: 829-838, 2006.

Jacquy et al. "Cerebral Blood Flow and Quantitative Rheoencephalography", Electroencephalographyand Clinical Neurophysiology, 37: 507-511, 1974.

Jevning et al. "Evaluation of Consistency Among Different Electrical Impedance Indices of Relative Cerebral Blood Flow in Normal Resting Individuals", Journal of Biomedical Engineering, XP022444925, 11(1): 53-56, Jan. 1, 1989.

Keren et al. "Evaluation of an Noninvasive Continuous Cardiac Output Monitoring System Based on Thoracic Bioreactance", American Journal of Physiology: Heart Circulation Physiology, 293: H583-H589, 2007.

Seoane Martinez "Electrical Bioimpedance Cerebral Monitoring: Fundamental Steps Toward Clinical Applications", Thesis for the Degree of Doctor of Philosophy, Department of Signals and Systems, Division of Biomedical Engineering, Chalmers University of Technology, Göteborg, Sweden & School of Engineering, University College of Borås, Borås, Sweden, 153 P., 2007.

Steiner et al. "Continuous Monitoring of Cerebrovascular Pressure Reactivity Allows Determination of Optimal Cerebral Perfusion Pressure in Patients With Traumatic Brain Injury", Critical Care Medicine, 30(4): 733-738, Apr. 2002. Abstract.

Stiefel et al. "Reduced Mortality Rate in Patients With Severe Traumatic Brain Injury Treated With Brain Tissue Oxygen Monitoring", Journal of Neurosurgery, 103(5): 805-811, Nov. 2005.

Notice of Allowance Dated Apr. 11, 2011 From the US Patent and Trademark Office Re.: U.S. Appl. No. 10/893,570.

International Preliminary Report on Patentability Dated Apr. 21, 2011 From the International Bureau of WIPO Re. Application No. PCT/IB2009/054388.

Response Dated Feb. 27, 2011 to Office Action of Aug. 12, 2010 From the State Intellectual Property Office of the People's Republic of China Re. Application No. 200780051314.2.

Translation of Office Action Dated Aug. 12, 2010 From the State Intellectual Property Office of the People's Republic of China Re. Application No. 200780051314.2.

Communication Pursuant to Article 94(3) EPC Dated Apr. 28, 2011 From the European Patent Office Re. Application No. 05752203.9.

International Search Report and the Written Opinion Dated Apr. 20, 2010 From the International Searching Authority Re.: Application No. PCT/IB2009/054388.

International Search Report and the Written Opinion Dated Apr. 20, 2010 From the International Searching Authority Re.: Application No. PCT/IB2009/054392.

Response Dated May 5, 2010 to Rejection Decision of Feb. 12, 2010 From the State Intellectual Property Office of the People's Republic of China Re.: Application No. 200580031089.7.

Lovett Doust et al. "Aspects of the Cerebral Circulation During Non-REM Sleep in Healthy Controls and Psychiatric Patients, as Shown by Rheoencephalography", Psychophysiology, XP002572590, 12(5): 493-498, 1975. Abstract, p. 494, r-h Col., § 2-p. 495, l-h Col., § 5, p. 495, l-h Col., § 1, p. 495, l-h col., § 5-r-h Col., § 1, p. 496, l-h Col., Fig. 1, Tables 1-2.

Communication Under Rule 71(3) EPC Dated May 18, 2011 From the European Patent Office Re.: Application No. 05750856.6.

Official Action Dated Apr. 13, 2011 From the US Patent and Trademark Office Re. U.S. Appl. No. 11/572,141.

Translation of Notification to Grant Patent Right for Invention Dated May 26, 2011 From the State Intellectual Property Office of the People's Republic of China Re. Application No. 200780051314.2.

Official Action Dated Feb. 20, 2009 From the US Patent and Trademark Office Re.: U.S. Appl. No. 10/893,570.

Communication Pursuant to Article 94(3) EPC Dated Jun. 2, 2010 From the European Patent Office Re. Application No. 05752203.9.

Official Action Dated Jun. 1, 2010 From the US Patent and Trademark Office Re.: U.S. Appl. No. 10/893,570.

Communication Pursuant to Article 94(3) EPC Dated Jun. 22, 2011 From the European Patent Office Re.: Application No. 07827394.3.

Translation of Notice of Reason for Rejection Dated Jun. 17, 2011 From the Japanese Patent Office Re. Application No. 2008-516457.
Official Action Dated Jun. 7, 2011 From the US Patent and Trademark Office Re. U.S. Appl. No. 11/572,157.
Bartocci et al. "Cerebral Blood-Flow Monitor for Use in Neonatal Intensive Care Units", Computer Methods and Programs in Biomedicine, 59: 61-73, 1999.
Colditz et al. "Continuous Cerebral Electrical Impedance Monitoring in Sick Preterm Infants", European Journal of Pediatrics, 149: 428-431, 1990.
Linderholm et al. "Imicroelectrical Impedance Tomography for Biophysical Characterization of Thin Film Biomaterials", Transducer '03, The 12th International Conference on Solid State Sensors, Actuators and Microsystems, Boston, Jun. 8-12, 2003, p. 284-287, Jun. 2003.
Response Dated May 31, 2011 to Notification of Reasons for Rejection of Dec. 14, 2010 From the Japanese Patent Office Re. Application No. 2007-520969.
Bellner et al. "Transcranial Doppler Sonography Pulsatility Index (PI) Reflects Intracranial Pressure (ICP)", Surgical Neurology, 62(1): 45-51, Jul. 2004.
Response Dated Jul. 18, 2010 to Communication Pursuant to Article 94(3) EPC of Feb. 24, 2010 From the European Patent Office Re.: Application No. 07827394.3.
Response Dated Jul. 19, 2010 to Communication Pursuant to Article 94(3) EPC of Mar. 29, 2010 From the European Patent Office Re.: Application No. 05750856.6.
Response Dated Jul. 26, 2010 to the Written Opinion of Dec. 23, 2009 From the International Searching Authority Re.: Application No. PCT/IB2009/054394.
Decision of Rejection Dated Jul. 28, 2011 From the Japanese Patent Office Re. Application No. 2007-520969 and Its Translation Into English.
Response Dated Jul. 19, 2011 to Notification of Reasons for Rejection of Mar. 22, 2011 From the Japanese Patent Office Re. Application No. 2007-520968.
Response Dated Aug. 9, 2010 to the Written Opinion of Apr. 20, 2010 From the International Searching Authority Re.: Application No. PCT/IB2009/054392.
Response Dated Jul. 29, 2010 to the Written Opinion of Apr. 20, 2010 From the International Searching Authority Re.: Application No. PCT/IB2009/054388.
Invitation to Restrict or Pay Additional Fees Dated Aug. 24, 2010 From the International Preliminary Examining Authority Re. Application No. PCT/IB2009/054388.

Response Dated Sep. 1, 2010 to Official Action of Jun. 1, 2010 From the US Patent and Trademark Office Re.: U.S. Appl. No. 10/893,570.
Response Dated Sep. 5, 2011 to Notice of Reason for Rejection of Jun. 17, 2011 From the Japanese Patent Office Re. Application No. 2008-516457.
Translation of Office Action Dated Jun. 5, 2009 From the State Intellectual Property Office of the People's Republic of China Re.: Application No. 200680029920.X.
Translation of Office Action Dated Aug. 7, 2009 From the State Intellectual Property Office of the People's Republic of China Re.: Application No. 200580031089.7.
Response Dated Oct. 3, 2010 to Communication Pursuant to Article 94(3) EPC of Jun. 2, 2010 From the European Patent Office Re. Application No. 05752203.9.
Communication Relating to the Results of the Partial International Search Dated Dec. 29, 2009 From the International Searching Authority Re.: Application No. PCT/IB2009/054388.
Grönlund et al. "High Frequency Variability of Trancephalic Electrical Impedance. A New Parameter for Monitoring of Neonatal Cerebral Circulation?", Proceedings of the Annual International Conference of the Engineering in Medicine and Biology Society, 6(Conf. 14): 2513-2515, 1992. p. 2513, r-h Col., Lines 6-20.
Grönlund et al. "Transephalic Electrical Impedance Provides a Means for Quantifying Pulsatile Cerebral Blood Volume Changes Following Head-Up Tilt", Early Human Development, 47: 11-18, 1997.
Decision to Grant a European Patent Pursuant to Article 97(1) EPC Dated Nov. 10, 2011 From the European Patent Office Re.: Application No. 05752203.9.
Response Dated Nov. 7, 2011 to Official Action of Jun. 7, 2011 From the US Patent and Trademark Office Re. U.S. Appl. No. 11/572,157.
Response Dated Nov. 16, 2011 to Decision of Rejection of Jul. 28, 2011 From the Japanese Patent Office Re. Application No. 2007-520969.
Official Action Dated Nov. 5, 2010 From the US Patent and Trademark Office Re.: U.S. Appl. No. 10/893,570.
Response Dated Oct. 11, 2011 to Official Action of Apr. 13, 2011 From the US Patent and Trademark Office Re. U.S. Appl. No. 11/572,141.
Response Dated Oct. 27, 2011 to Communication Pursuant to Article 94(3) EPC of Jun. 22, 2011 From the European Patent Office Re.: Application No. 07827394.3.
Response Dated Oct. 27, 2011 to Communication Pursuant to Article 94(3) EPC of Apr. 28, 2011 From the European Patent Office Re. Application No. 05752203.9.

* cited by examiner

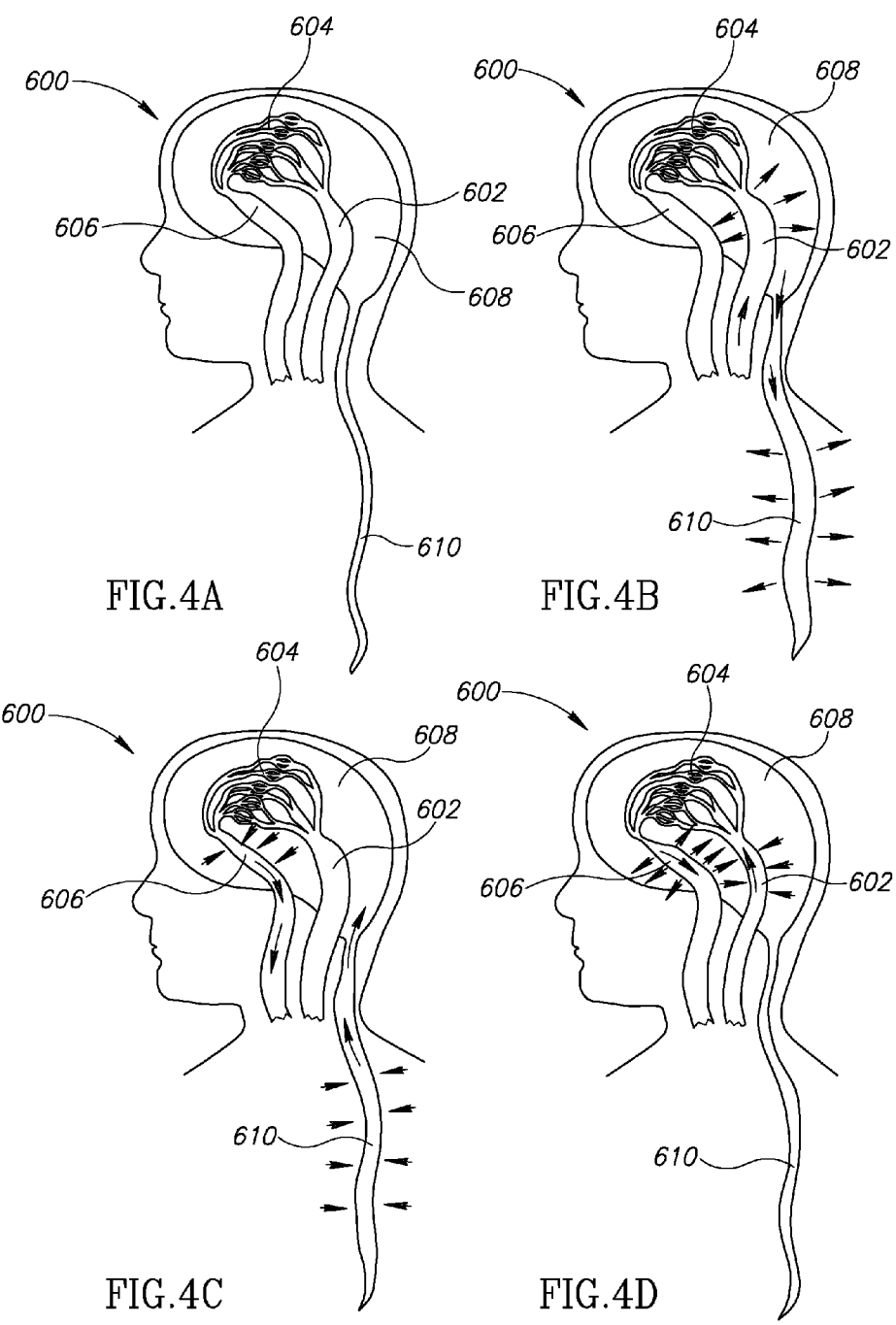

NON-INVASIVE INTRACRANIAL MONITOR

RELATED APPLICATIONS

The present application claims priority from, and is a continuation-in-part of PCT/IB2006/050174, filed Jan. 17, 2006, which is a continuation-in-part of two related PCT patent applications PCT/IL2005/000631 and PCT/IL2005/000632, both filed Jun. 15, 2005. Those PCT applications are both continuations-in-part of U.S. patent application Ser. No. 10/893,570, filed Jul. 15, 2004 now U.S. Pat. No. 7,998,080, which is a continuation-in-part of PCT patent application PCT/IL03/00042, filed Jan. 15, 2003, which claims benefit under 35 USC 119(e) from U.S. provisional patent application 60/348,278, filed Jan. 15, 2002. The disclosures of all of these applications are incorporated herein by reference.

FIELD OF THE INVENTION

The field of the invention is estimating intracranial parameters by using bio-impedance.

BACKGROUND OF THE INVENTION

Intracranial pressure (ICP), and other intracranial hemodynamic parameters, are important for diagnosing a variety of medical conditions involving the central nervous system, and for monitoring their treatment. The most commonly used methods for measuring ICP are invasive, involving inserting a probe into the central nervous system space. Such methods can be dangerous, because they carry a risk of infection or hemorrhage, and they can be inaccurate. Inaccuracies can result from obstruction of the fluid in an external strain gauge, or from poor maintenance of a reference point with external transducers, or from calibration issues when fiberoptic devices are used.

Several patents and published applications, including US 2004/0049105 to Crutchfield et al, US 2006/0094964 to Ragauskas, U.S. Pat. No. 4,984,567 to Kageyama, U.S. Pat. No. 6,117,089 to Sinha, MXPA01011471 to Inta Medics, Ltd. (Israel), and U.S. Pat. No. 6,875,176, suggest the use of ultrasound to indirectly determine ICP in a non-invasive manner. A similar method using MRI is suggested by U.S. Pat. No. 6,245,027 to Alperin.

Although methods involving ultrasound and MRI are non-invasive, they require expensive equipment, and skilled personnel to interpret the results. Hence, they are not practical for continuous monitoring of ICP in patients.

U.S. Pat. No. 6,773,407 describes measuring ICP by temporarily raising it a known amount, and directly measuring the resulting increase in volume of the skull. EP0020677 describes temporarily occluding the jugular vein, and determining ICP by observing the response upstream. These methods may also not be practical for continuous monitoring of ICP, because they may cause some danger or discomfort to the patient.

There are methods of continuously monitoring ICP non-invasively. U.S. Pat. No. 7,041,063 describes an optical sensor mounted on the outside of the cornea, which can detect ICP by its effect on swelling of the retina and the optic nerve head. Russian patent publication RU2185091, to Zabolotskikh et al, describes measuring ICP non-invasively by measuring blood pressure in the central retinal vein. U.S. Pat. No. 6,976,963 uses periodic swelling of the external auditory canal, at the cardiac frequency, to measure the pulse waveform of the blood pressure, and uses that to infer, among other things, ICP. Russian patent publication RU2163090 to Bokhov et al measures ICP by measuring the mechanical tension in the tympanic membrane at auditory frequencies. U.S. Pat. No. 5,040,540 to Sackner describes a mechanical transducer on the neck, which non-invasively measures central venous blood pressure in infants, and uses that to infer ICP, using the known relation between central venous pressure and ICP. However, it is difficult to measure central venous pressure non-invasively in adults, without access to large veins.

U.S. Pat. No. 6,491,647 to Bridger et al describes a mechanical external (non-invasive) blood pressure sensor which can be used, among other uses, for assessing blood flow in the temples of patients with elevated ICP. Using this kind of mechanical blood pressure sensor is described as superior to using bio-impedance methods, or photoplethysmography, for measuring blood flow. Bridger et al does not describe methods of measuring ICP.

Rheoencephalography (REG) is a technique that uses bio-impedance measurements of the head to obtain information on about cerebral blood circulation and circulatory problems. Generally, changes in impedance Z across the head, for a particular arrangement of electrodes, are measured as a function of time t over a cardiac cycle, and sometimes over a breathing cycle, due to changes in the volume and distribution of blood in the head. As described by W. Traczewski et al, "The Role of Computerized Rheoencephalography in the Assessment of Normal Pressure Hydrocephalus," *J. Neurotrauma* 22, 836-843 (2005), REG is commonly used to measure or diagnose problems with circulatory resistance, and problems with arterial elasticity. In patients with normal pressure hydrocephalus, for example, Traczewski et al find two different patterns in Z(t), depending on the elasticity of the small cerebral arteries. The pattern of Z(t) seen in a given patient can be used to make predictions about the likely outcome of different treatments for the hydrocephalus. These patients all had similar, normal values of ICP.

WO 06/006143 and WO 06/011128 to Shapira et al, and US 2005/0054939 and WO 03/059164 to Ben-Ari et al, describe the use of REG to monitor cerebral blood flow, for example in order to detect sudden decreases in cerebral blood flow rate. Specially designed electrodes, and supplementary information from photoplethysmography (PPG), are optionally used to make the bio-impedance measurements more sensitive to cerebral blood flow, and less sensitive to peripheral blood flow in the head. WO 03/059164 describes using the change in impedance of the head over a cardiac cycle as an indicator of cerebral blood flow. WO 06/011128 describes using the rate of change in impedance following the diastole as an indicator of cerebral blood flow.

J. Gronlund, J. Jalonen, and I. Valimaki, "Transcephalic electrical impedance provides a means for quantifying pulsatile cerebral blood volume changes following head-up tilt," *Early Human Development* 47 (1997) 11-18, describe electrical impedance measurements of the head in premature newborn infants. Changes in impedance associated with the cardiac cycle are said to reflect changes in total cerebral blood volume, and earlier papers are referenced which are said to demonstrate this. Variability in impedance, in the range of 1.5 to 4 Hz, was found to decrease by 27%, on average, when the infants' heads were tilted up by 20 degrees.

Low cerebral blood flow is caused by low cerebral perfusion pressure (CPP), which is the difference between cranial intra arterial pressure (CIAP) and ICP. A low value of CPP may be due to either high ICP, or low CIAP. Low CIAP, in turn, may be due to 1) a systemic problem such as low mean arterial pressure (MAP), caused for example by a cardiac problem, or it may be due to 2) a blockage or hemorrhage of an artery in or leading to the head, resulting in a CIAP that is lower than the MAP. Monitoring MAP is a useful method for detecting the first set of conditions, but may not be useful for detecting the second set of conditions.

Czosnyka et al, J Neurosurg 1998; 88:802-8 describes the use of transcranial Doppler (TCD) ultrasound to estimate CPP non-invasively, but this technique is not practical to use for continuous monitoring.

Total cerebral blood volume (CBV) may be useful for diagnosing hemorrhagic strokes, and for diagnosing problems caused by traumatic brain injury. Positron emission tomography (PET) has been used to measure CBV. Wintermark et al, Stroke 2005; 36:e83-e99 describes the use of perfusion computed tomography (PCT) for measuring CBV. These techniques are also not practical for continuous monitoring of patients. It is known that changes in electrical impedance of the head are an indication of changes in cerebral blood volume; see, for example, Traczewski et al, cited above.

All of the patents and other publications cited above are incorporated herein by reference.

SUMMARY OF THE INVENTION

An aspect of some exemplary embodiments of the invention concerns using measurements of the variation with time of the bio-impedance Z of the head, during the cardiac cycle, to estimate intracranial parameters, optionally in addition to cerebral blood flow, cerebral circulatory resistance, and cerebral arterial elasticity, including ICP, cerebral blood volume (CBV), and a factor relating to CPP and/or a mean transit time of blood through cerebral capillaries (MTT). In an exemplary embodiment of the invention, the shape of Z(t), where t is the time, optionally normalized to a measure of the range of Z and/or to the heart rate, is used to calculate one or more indicators, which provide estimates of one or more of the intracranial parameters. Such an indicator may provide an estimate of the absolute level of an intracranial parameter, or a change in the value of an indicator may provide an estimate of the change in the level of an intracranial parameter, relative to a baseline level.

It should be noted that, conventionally, in the bio-impedance literature, the negative of the impedance is commonly referred to as the impedance, or Z, so a higher Z means a greater cerebral blood volume. This convention has been adopted here, in the specification and the claims.

Generally, for subjects with either normal or abnormal intracranial parameters, the impedance Z has a minimum at a time close to the diastolic phase of the cardiac cycle, a first peak close to the systolic phase of the cardiac cycle, and a second peak after the systolic phase. The inventors have discovered that the relative heights of these first and second peaks may be used as an indicator of a factor related to CPP and/or MTT. Optionally, subjects with this factor lower than normal, i.e. with lower than normal CPP, or higher than normal MTT, are distinguished by having the second peak higher than the first peak, while in subjects with normal CPP and MTT, the first peak is greater than the second peak. Optionally, the heights of the first and second peaks relative to the minimum impedance are used to estimate the factor related to CPP and/or MTT, absolutely or relative to a baseline. For example, the ratio of the heights of the first and second peaks is used as an indicator of the factor related to CPP and/or MTT, or the ratio of the height of the first peak to the height of the higher of the two peaks is used.

It should be noted that generally, and in particular for the tests done by the inventors, CPP has an inverse relation with MTT, i.e. CPP is lower than normal when MTT is higher than normal, and vice versa. It is not always clear whether the factor related to CPP and/or MTT is actually measuring CPP, or MTT, or a combination of the two. Henceforth, we will only refer to indicating or measuring CPP, but it should be understood that the methods described are actually indicating a factor which may, in fact, depend on MTT, instead of or in addition to CPP.

The inventors have also discovered other characteristics of Z(t) that may be used as indicators of CPP, CBV, or ICP, as will be described in the following paragraphs.

For example, alternatively or additionally, CPP is estimated from a rate of rise of Z(t), for example a characteristic maximum rate of rise of Z(t) during a cardiac cycle, optionally normalized to the full range of Z(t). By "characteristic maximum rate of rise" is meant a number which is less sensitive to noise and artifacts than the maximum rate of rise of the raw Z(t), for example the maximum rate of rise of Z(t) after smoothing, and/or after outliers in the data have been removed. "Characteristic rate of fall" and "characteristic range" of Z(t) are defined in a similar manner. Optionally, a rate of rise of Z(t) is combined with a ratio of the heights of the first and second peaks of Z(t), for example by finding a weighted average of the two, to obtain an indicator of CPP that is more accurate than either of the two individual indicators.

Optionally, a characteristic maximum rate of fall of Z(t) is used to estimate ICP or CBV. The maximum rate of fall is often observed to occur after the second peak in Z(t). Optionally, the maximum rate of fall after the second peak, or an average rate of fall following the second peak, is used to estimate ICP or CBV.

Optionally, a peak to peak range of Z(t), or a characteristic measure of the range of Z(t), is used to estimate ICP or CBV. Even if there is a large spread in the range of Z(t) for different subjects with normal ICP and CBV, changes in the range of Z(t) from a baseline value, during a single measurement session on a given subject, may still be useful for real time detection of changes in ICP or CBV.

In some embodiments of the invention, ICP is estimated from characteristics of Z(t) which provide information about the compliance of cerebral arteries. In patients with elevated ICP, the arteries are expected not to be able to expand as rapidly in response to changes in intra arterial pressure, so the cerebral arteries are effectively less compliant, and a pressure wave propagates more rapidly through them as the heart contracts. This results in a shorter time difference between the diastolic time, as indicated by the minimum in Z(t) or by the peak ECG signal, and the time of maximum rate of rise of Z(t). This time difference may be used as an indicator of ICP, with a shorter time difference corresponding to higher ICP.

In some embodiments of the invention, estimates of one or more of the intracranial parameters are used to diagnose medical conditions. In particular, knowing one or more of the intracranial parameters may be useful for distinguishing between different conditions which present similar clinical symptoms, but which call for different methods of treatment.

For example, hemorrhagic stroke may be characterized by high CBV and ICP, while ischemic stroke may be characterized by low or unchanged CBV and ICP. Both types of stroke are also characterized by low CPP. Traumatic brain injury is generally characterized by high ICP and low CPP, and by high, normal, or low CBV, depending on how much hemorrhaging occurs. Cerebral tumors, and brain infections may also be characterized by high CBV and ICP, and low CPP. Using impedance measurements to rapidly estimate these parameters in stroke patients, trauma patients, and others, may allow appropriate treatment to begin early, when it is most useful. Continued monitoring of head impedance during treatment can provide timely information about the effectiveness of treatment, and about the continuing development of a stroke, or a brain injury, in real time. For example, such monitoring can provide immediate warning if anticoagulants or clot dissolving drugs, administered to an ischemic stroke patient, are causing cerebral hemorrhaging and should be discontinued or reduced in dosage.

In patients undergoing endarterectomy surgery, blood flow in some arteries may be cut off for a period of time. In other types of surgery, as well as in other clinical situations such as shock or cardiac problems, there is a danger of a fall in central MAP, which can also reduce CPP. Monitoring impedance of the head, and using Z(t) to estimate intracranial parameters in real time, may warn the surgeon or treating physician if cerebral blood flow falls to dangerously low levels, allowing intervention in time to avoid serious neurological damage.

There are also patients with chronic conditions who can benefit from monitoring of intracranial parameters estimated from head impedance, including patients suffering from cerebrovascular diseases, dementia, and migraines. Monitoring such patients may help to provide prognosis of treatments being used, allowing the selection of patients with worse prognosis for whom more aggressive, and riskier, treatment may be appropriate.

Monitoring of intracranial parameters in neonatal and premature infants may be particularly useful, since such infants may not have a fully developed cerebral autoregulation system. Relatively small disturbances in MAP, caused for example by suctioning, insertion of intravenous catheters, or blood sampling, which would not affect cerebral blood flow in more mature individuals, may cause a serious change (increase or decrease) in CPP in such infants, which can be treated if detected immediately.

There is thus provided, according to an exemplary embodiment of the invention, a method of estimating at least one intracranial hemodynamic parameter in a subject, the method comprising:
 a) obtaining data of changes in electrical impedance across the subject's head as a function of time;
 b) analyzing the data; and
 c) estimating one or more of intracranial pressure, cerebral blood volume, and a factor related to at least one of cerebral perfusion pressure and mean transit time through the capillaries.

Optionally, analyzing the data comprises one or more of smoothing the data, removing variations in the data due to the subject's breathing cycle, and selecting data only from a portion of the subject's cardiac cycles.

In an embodiment of the invention, analyzing the data comprises finding a measure of the range of impedance, and estimating comprises estimating one or more of intracranial pressure and cerebral blood volume, responsive to the measure of the range of impedance.

Alternatively or additionally, analyzing the data comprises finding a measure of a maximum rate of fall of the impedance, and estimating comprises estimating one or more of intracranial pressure and cerebral blood volume, responsive to the measure of the maximum rate of fall.

In an embodiment of the invention, analyzing the data comprises finding a measure of a maximum rate of rise of the impedance, and estimating comprises estimating a factor related to one or more of cerebral perfusion pressure and mean transit time through the capillaries, responsive to the measure of the maximum rate of rise.

In an embodiment of the invention, analyzing the data comprises finding a measure of a height of a first local maximum of impedance, or a first local minimum in rate of rise of impedance, following the diastolic phase of the cardiac cycle, and estimating comprises estimating a factor related to one or more of cerebral perfusion pressure and mean transit time through the capillaries, responsive to the measure of the height of the first local maximum, or minimum in rate of rise, of impedance.

Optionally, analyzing the data comprises normalizing the measure of the height of the first local maximum, or minimum in rate of rise, of impedance to a measure of a height of a second local maximum in impedance, following the diastolic phase of the cardiac cycle and the first local maximum, or minimum in rate of rise, of impedance.

Optionally, the factor is related to cerebral perfusion pressure. Alternatively or additionally, the factor is related to mean transit time through the capillaries.

Optionally, analyzing the data also comprises finding a measure of a maximum rate of rise of the impedance, and estimating the factor related to one or more of cerebral perfusion pressure and mean transit time through the capillaries is responsive to a combination of the measure of a maximum rate of rise of the impedance, and the measure of a first local maximum in impedance or first local minimum in rate of rise of impedance.

Optionally, analyzing the data comprises normalizing to a measure of the total range of impedance.

In an embodiment of the invention, analyzing the data comprises finding a measure of a latency time, and estimating comprising estimating intracranial pressure responsive to the measure of the latency time.

Optionally, analyzing the data comprises normalizing time to a cardiac period. Optionally, analyzing the data comprises smoothing of data over time. Optionally, analyzing the data comprises finding a measure of the at least one intracranial parameter and averaging the measure over a plurality of cardiac cycles. Optionally, analyzing the data comprises averaging data from a same phase of different cardiac cycles. Optionally, analyzing the data comprises excluding values of impedance, or values of rate of change of impedance, or both, that do not fall within an expected range of magnitude or do not occur within an expected range of time relative to the cardiac cycle, or both.

In an embodiment of the invention, the at least one hemodynamic parameter is monitored substantially continuously for a subject undergoing surgery.

Alternatively or additionally, the at least one hemodynamic parameter is monitored substantially continuously for a subject who is a stroke patient.

Alternatively or additionally, the at least one hemodynamic parameter is monitored substantially continuously for a subject suffering from a traumatic head injury.

Alternatively or additionally, the at least one hemodynamic parameter is monitored substantially continuously for a subject suffering from a chronic condition.

In an embodiment of the invention, the at least one hemodynamic parameter is monitored substantially continuously for a subject who is a neonate.

There is further provided, in accordance with an exemplary embodiment of the invention, apparatus for estimating one or more intracranial hemodynamic parameters, the apparatus comprising:
 a) a device for obtaining electrical impedance data of the head as a function of time relative to the timing of the cardiac cycle; and
 b) a controller configured to estimate at least one of intracranial pressure, cerebral blood volume, and a factor related to one or more of cerebral perfusion pressure and mean transit time through the capillaries, from the data.

Optionally, the controller is configured to analyze the data to find a measure of the range of impedance, and to estimate one or more of intracranial pressure and cerebral blood volume, responsive to the measure of the range of impedance.

Alternatively or additionally, the controller is configured to analyze the data to find a measure of a maximum rate of fall of impedance, and to estimate one or more of intracranial pressure and cerebral blood volume, responsive to the measure of the maximum rate of fall of impedance.

In an embodiment of the invention, the controller is configured to analyze the data to find a measure of a maximum rate of rise of impedance, and to estimate a factor related to one or more of cerebral perfusion pressure and mean transit time, responsive to the measure of the maximum rate of rise of impedance.

Alternatively or additionally, the controller is configured to analyze the data to find a measure of a height of a first local maximum in impedance, or a first local minimum in rate of rise of impedance, following the diastolic phase of the cardiac cycle, and to estimate a factor related to one or more of cerebral perfusion pressure and mean transit time, responsive to the measure of the height of the first local maximum, or minimum in rate of rise, of impedance.

In an embodiment of the invention, the controller is configured to analyze the data to find a measure of a latency time, and to estimate intracranial pressure, responsive to the measure of the latency time.

BRIEF DESCRIPTIONS OF THE DRAWINGS

Exemplary non-limiting embodiments of the invention are described in the following sections with reference to the drawings. The drawings are generally not to scale and the same or similar reference numbers are used for the same or related features on different drawings.

Figure 2A:
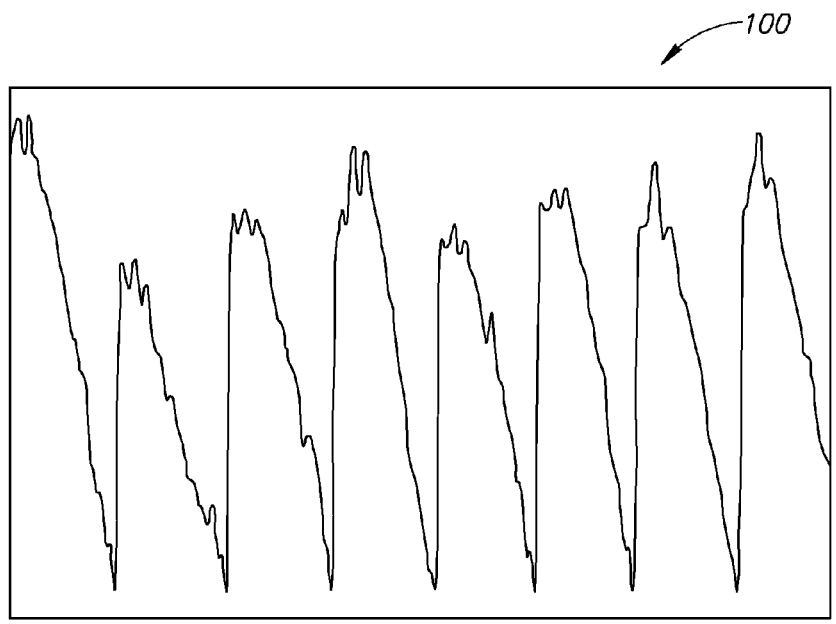
Figure 2B:
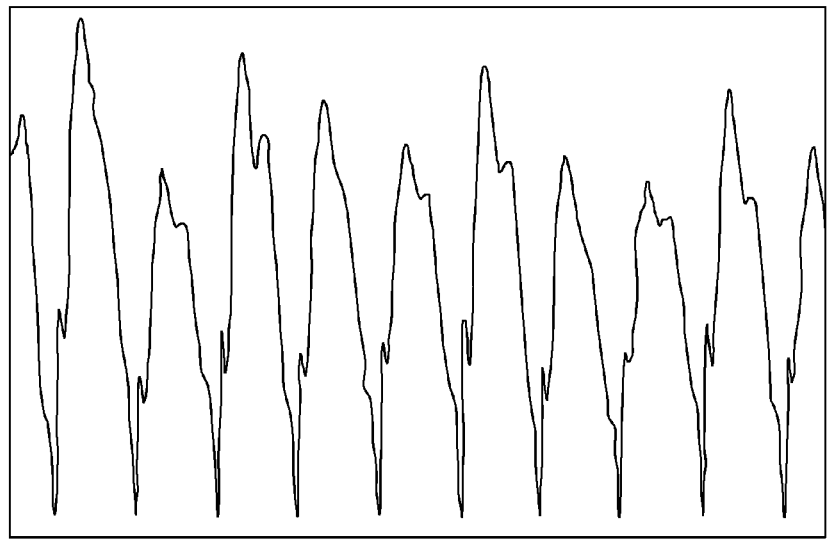
Figure 3A:
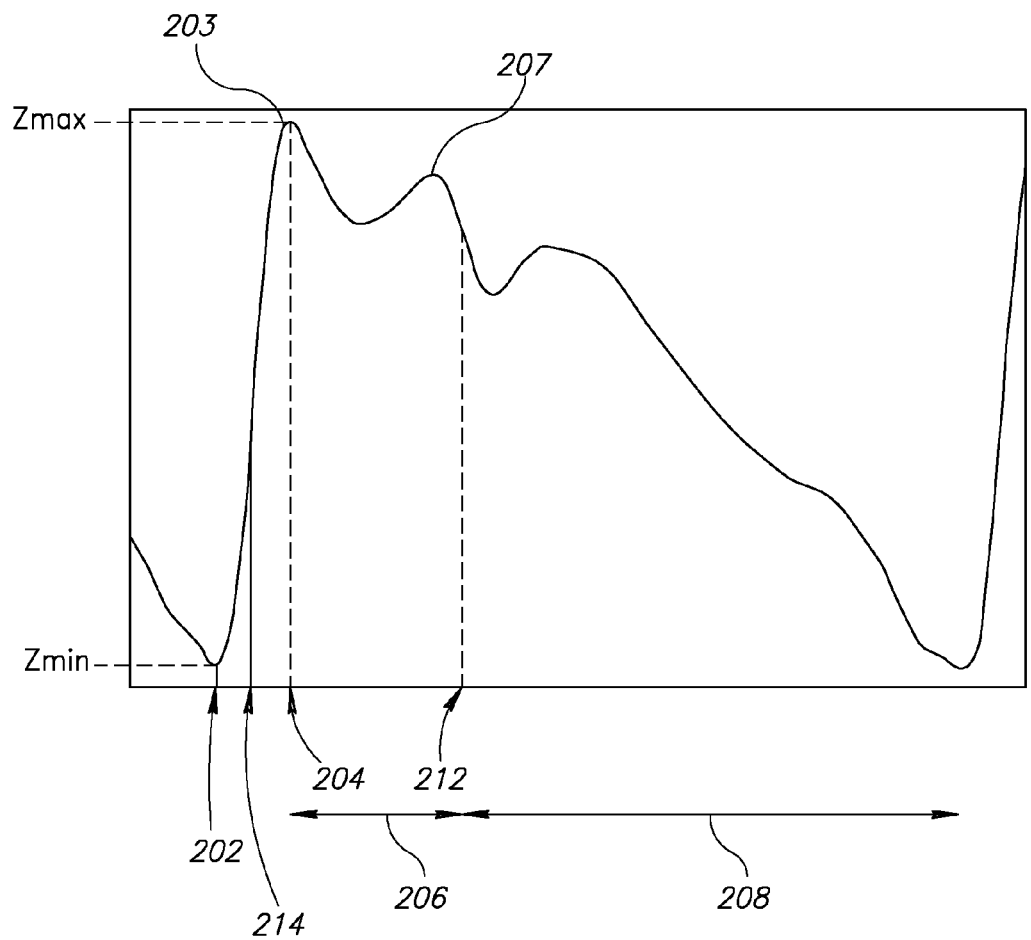
Figure 3B:
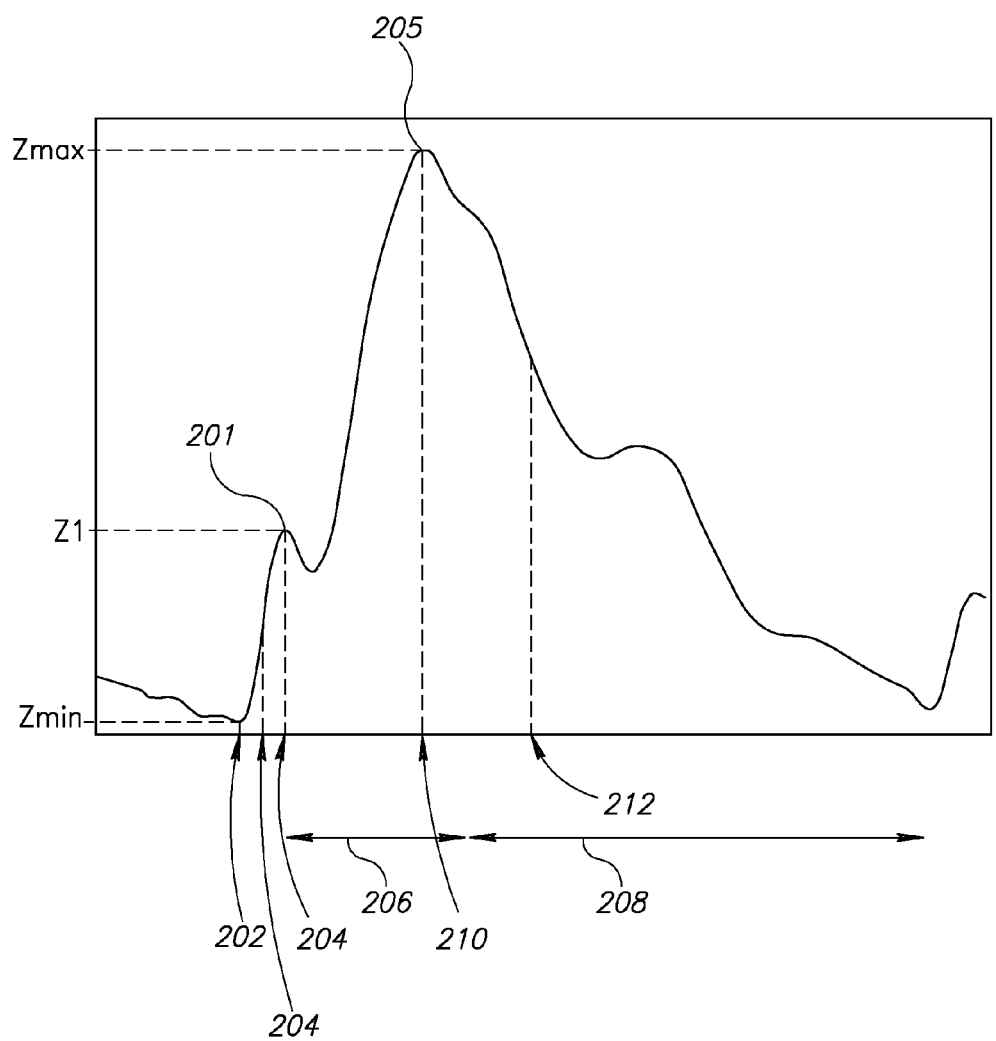
Figure 5:
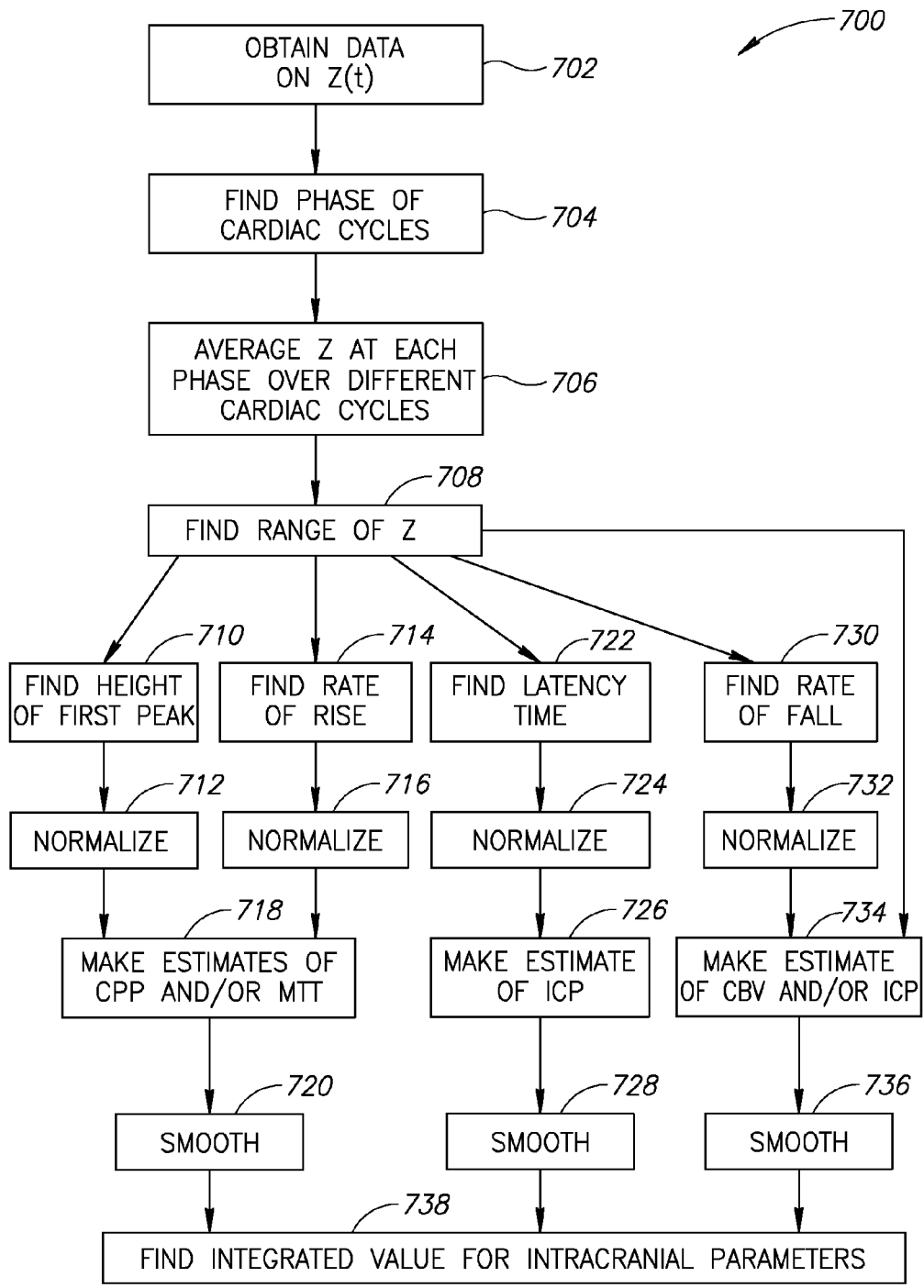
Figure 6:
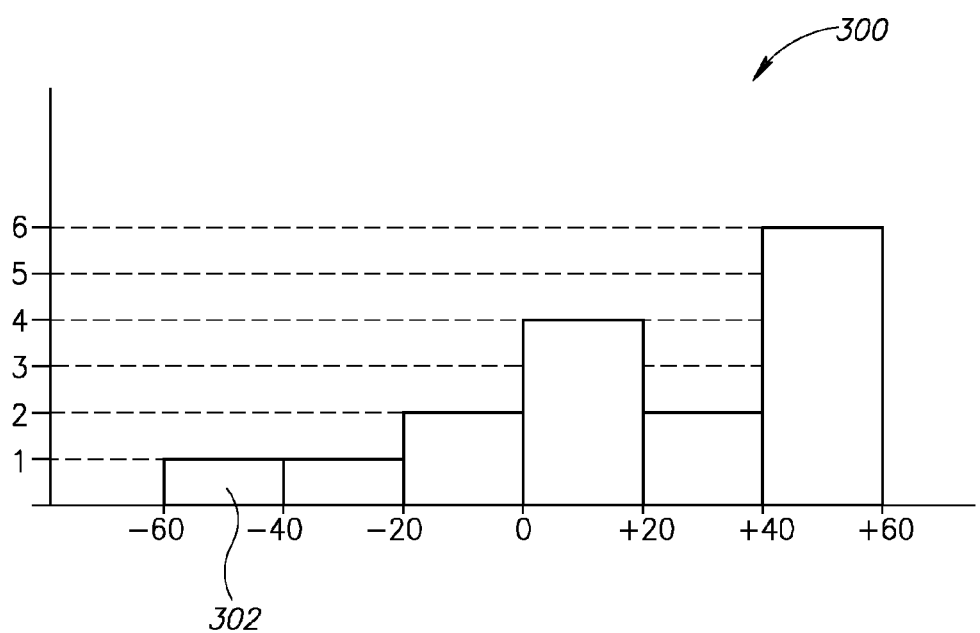

FIG. 1 schematically shows a system for using bio-impedance to estimate intracranial parameters, according to an exemplary embodiment of the invention;

FIGS. 2A and 2B schematically show plots of electrical impedance measured across the head as a function of time during several cardiac cycles, respectively for a subject with normal CPP and for a subject with low CPP, according to an exemplary embodiment of the invention;

FIGS. 3A and 3B respectively show more detailed views of the plots shown in FIGS. 2A and 2B, for a single cardiac cycle;

FIGS. 4A-4D schematically show side cross-sections of the head and neck, at different times during a cardiac cycle, illustrating a possible model for how artery volume changes during the cardiac cycle;

FIG. 5 shows a flowchart for estimation of intracranial parameters from bio-impedance data, according to an exemplary embodiment of the invention; and FIG. 6 is a graph showing the distribution of values of an indicator of cerebral perfusion pressure for patients undergoing an endarterectomy procedure, according to an exemplary embodiment of the invention.

DETAILED DESCRIPTION OF EXEMPLARY EMBODIMENTS

FIG. 1 schematically shows a system 500 for estimating one or more intracranial parameters in a subject 502, using bio-impedance measurements of the subject's head, according to an exemplary embodiment of the invention. A system controller 512, for example a computer, uses data of the impedance measurements to estimate the intracranial parameters, and outputs the result, for example by displaying it on a monitor 514.

Electrodes 504 are placed on the subject's head in order to measure the impedance of the head. Electrodes 504 may use any design for bio-impedance electrodes known to the art, including the designs described in WO 06/006143 and WO 06/011128 to Shapira et al, and US 2005/0054939 and WO 03/059164 to Ben-Ari et al. For example, there may be separate current and voltage electrodes. Although FIG. 1 only shows two electrodes 504, there may be more than two electrodes. The electrodes may be placed on the head at any of the locations suggested in the prior art for bio-impedance measurements of the head, including the published applications mentioned above.

A bio-impedance device controller 506 includes a power supply which supplies current to electrodes 504, typically AC current, at least for safety reasons. The frequency of the AC current is typically between 20 kHz and 100 kHz, for example, as described in the above mentioned published applications, but may be higher or lower. Controller 506 also measures voltage across two or more of electrodes 504, not necessarily the same electrodes that controller 506 supplies current to. Optionally, controller 506 calculates the impedance Z of the head by dividing the voltage by the current. The impedance Z is measured at a plurality of different times t. Optionally, the times are chosen according to the phase of the cardiac cycle, as determined for example from an ECG (not shown), or the phases of the cardiac cycle corresponding to the different times are found after the impedance measurements are made. Optionally, data on Z(t), generated by bio-impedance controller 506, is transmitted to system controller 512. Optionally, impedance data Z is also measured at different times corresponding to different phases in the breathing cycle. Optionally, the subject holds his breath when data on Z(t) is obtained, in order to separate the dependence on the cardiac cycle from the dependence on the breathing cycle. Optionally, software is used to separate the dependence of Z on the cardiac cycle from the dependence on the breathing cycle, for example by binning.

Optionally, either of controllers 506 and 512 is a physically separate unit, or is a module combined with the other controller, or a software module running on a same computer as the other controller. Either of the controllers may comprise digital processors, for example, or electronic circuits which produce similar results in an analog manner.

System controller 512 uses the impedance data Z(t), and optionally uses the ECG and/or breathing data, to estimate one or more intracranial parameters of subject 502, using any of the methods described below, alone or in combination. Optionally, the intracranial parameters are displayed on a monitor 514. The impedance data Z(t), the ECG data and/or the breathing data may also optionally be displayed.

FIGS. 2A and 2B show plots 100 and 102 of Z(t), measured across the head of a subject with normal ICP and CPP (FIG. 2A), and a subject with elevated ICP and low CPP (FIG. 2B). The plots show several cardiac cycles, and show only the dependence on the cardiac cycle, not on the breathing cycle modulation, which was digitally removed from the data. The change in blood volume and distribution in the head during each cardiac cycle is believed to be the main cause of the variation in Z(t) shown in FIGS. 2A and 2B, because blood is a better electrical conductor than other tissue in the head. As will be described, differences in the shape of Z(t) for subjects with normal and low CPP can be used to judge whether and to what extent CPP is reduced.

In describing FIGS. 2A-3B, the terms "blood volume," "impedance," and "Z" will be used interchangeably. But it should be understood that the "blood volume" measured in this way may be weighted very unevenly with respect to different blood vessels in the head. In particular, as will be described in more detail below following the description of FIGS. 3A-3B and 4A-4D, changes in impedance over the cardiac cycle may be most sensitive to the volume of the large arteries of the head, and less sensitive to the volume of veins and smaller arteries.

FIG. 3A shows Z(t) for a single cardiac cycle, for the data plotted in FIG. 2A for a subject with normal ICP and CPP, while FIG. 3B shows Z(t) for a single cardiac cycle for the data plotted in FIG. 2B for a subject with elevated ICP and hence low CPP. One way to distinguish Z(t) in the two cases is by the relative heights of the first two peaks in Z(t), following the minimum in Z(t). In FIG. 3A, a first peak 203 is higher than a second peak 207, while in FIG. 3B, a first peak 201 is lower than a second peak 205. This particular difference in Z(t) is believed to be associated with differences in CPP, for reasons explained below. Other differences in Z(t), associated with differences in CPP, ICP, and possibly CBV, will be described later.

Without being limited to any one explanation, this behavior of Z(t) in patients with normal CPP (FIG. 3A) and low CPP (FIG. 3B) will be described according to a particular model which appears to be consistent with the observations. The model will be illustrated using FIGS. 4A-4D, which schematically show a head 600 with an artery 602, representing the large arteries of the head, connected by capillaries 604 to a vein 606, representing the cerebral veins, a cranial cavity 608 filled with CSF, and a spinal channel 610 connected to the cranial cavity. Changes in impedance Z(t) primarily reflect changes in the volume of blood in the large arteries, such as artery 602, according to this model. It should be understood that the methods described for using Z(t) to estimate CPP have support from clinical data, and their validity does not necessarily depend on the extent to which this particular model is correct.

To begin with, we will assume that the patient with normal CPP (FIG. 3A) and the patient with low CPP (FIG. 3B) both have normal CIAP, so the difference between the two patients is that the patient with low CPP has elevated ICP. Then, we will show that similar differences in Z(t) are expected for the two patients if they both have the same ICP, but the patient with normal CPP has higher CIAP than the patient with low CPP.

In FIG. 3A, the blood volume is at a minimum, corresponding to a minimum impedance $Z_{min}$, at time 202, at the diastolic phase of the cardiac cycle, when the arterial blood pressure is at a minimum. FIG. 4A shows the head at this time.

As the arterial blood pressure increases due to the contraction of the heart, the blood volume in the arteries increases, because the arteries expand elastically, as shown in FIG. 4B. The arterial blood volume reaches a peak value, corresponding to impedance $Z_{max}$, labeled 203 in FIG. 3A, at time 204, at the systolic phase of the cardiac cycle, when the arterial blood pressure is at a maximum. When the arteries expand, they push against the CSF inside the cranial cavity, increasing the ICP. It is generally believed that the changes in cerebral arterial volume are compensated by movement of CSF between the cranial cavity and the spinal column, and by changes in venous volume, both mediated by changes in ICP. In the particular model illustrated in FIGS. 4A-4D, the CSF responds much more quickly to the increased ICP, moving into the spinal column, as shown in FIG. 4B, while the venous volume, exemplified by vein 606, initially remains almost unchanged. Because the ICP is not elevated to begin with, spinal cavity 610 is able to expand, in response to a relatively modest increase in ICP, to accommodate the change in volume of the arteries.

During the rapid rise in artery pressure from the diastolic to systolic phase, there is not enough time for very much blood to flow from the cerebral veins to the neck and trunk. How much the arterial blood volume increases, and how much Z rises, thus depends largely on how easily the spinal cavity can expand to accommodate the increase in arterial blood volume, which in turn depends on the ICP.

During time interval 206 following the systolic phase, the cerebral veins, such as vein 306, are compressed by the ICP, forcing blood that was in the veins to flow out of the head, as shown in FIG. 4C. The decrease in volume of the veins reduces the ICP, so there is less pressure outside the arteries, while the blood pressure inside the arteries goes down as more blood flows through the capillaries. As a result, the volume of the arteries only goes down slowly, during time interval 206, as shown in FIG. 4C. The volume of the arteries, and the impedance Z, often does not go down monotonically, but falls at first, then rises to second peak 207, which is lower than first peak 203 at the systolic phase, and then falls again. One possible explanation for this non-monotonic decrease in impedance is that the contraction of the heart generates a pressure wave which travels along the carotid arteries from the heart, past the cerebral arteries, and then reflects from the interface between the arteries and the capillaries, where there is an acoustic impedance mismatch. The reflected pressure wave travels back past the cerebral arteries, causing them to expand a second time, according to this explanation. This oscillatory behavior, whatever its cause, is superimposed on the overall slow downward trend in Z(t) during time interval 206.

Later, during time interval 208, the ICP is close to its minimum value, while the blood pressure inside the arteries continues to decrease as more blood goes through the capillaries into the veins. The volume of the arteries shrinks back down to the size it had at the diastolic phase at the beginning of the cardiac cycle, as shown in FIG. 4D. Meanwhile, the cerebral veins, such as vein 606, receive the blood from the capillaries, and the blood in the veins no longer flows as quickly out of the head, because the veins are not compressed as much by the ICP. Hence the cerebral veins start to expand again. Because the arteries shrink down rather slowly, according to this model, compared to the speed at which they expand earlier in the cardiac cycle, the veins have enough time to adjust their volume to compensate for the changing volume of the arteries, with little or no change in the ICP or the volume of the spinal cavity. There may also be one or more oscillations in Z(t), superimposed on the fall in Z(t), during interval 208, possibly with the same cause as the non-monotonic behavior of Z(t) during interval 206.

In FIG. 3B, the blood volume is again at its minimum at time 202, at the diastolic phase. As the arterial blood pressure increases due to the contraction of the heart, the arteries expand elastically, and the blood volume rises. The expanding arteries press against the CSF, increasing the ICP. But unlike in FIG. 3A, the ICP is elevated to begin with, so the spinal cavity is less compliant, and not as much CSF can flow into the spinal cavity. As a result, the arteries expand more slowly, and the blood volume (and impedance Z) reaches a lower first peak, corresponding to impedance $Z_1$, labeled 201 in FIG. 3B, at time 204, at the systolic phase of the cardiac cycle. During time interval 206, as more venous blood flows out of the head, the ICP decreases, relieving the pressure on the arteries, and the arteries start to expand again. The impedance Z increases correspondingly, reaching second peak 205 at a maximum value $Z_{max}$, at time 210. Even if the blood pressure inside the arteries is also decreasing during time interval 206, it is not decreasing as quickly as the ICP outside the arteries, so the arteries expand during this interval. During time interval 208, the ICP is close to its minimum value, and the blood pressure inside the arteries continues to decrease, so the arteries shrink back down to their minimum volume at the diastolic phase, and the impedance Z falls back down to $Z_{min}$.

If the ICP is elevated, but the CIAP is also elevated, so that CPP is normal, then the arteries will be able to expand more, as in FIG. 4B, because the higher pressure inside the arteries can force them to expand, producing a higher pressure in the CSF, forcing the spinal cavity to expand more in spite of its lower compliance. In this case, Z(t) will look similar to FIG. 3A. Conversely, if ICP is normal, but CIAP is reduced, then the arteries will not be able to expand very much until the venous blood starts to flow out of the head, after the systolic time, and Z(t) will look similar to FIG. 3B. Thus, the shape of Z(t) will depend more on the CPP, than on the ICP or the CIAP separately. However, it is possible that the shape of Z(t) will not depend exactly on the difference between ICP and CIAP, as CPP does, but will depend on a weighted difference of ICP and CIAP, or a similar nonlinear function of ICP and CIAP.

It should be noted that the shape of Z(t) seen in FIG. 3B, with second peak 205 higher than first peak 201, for patients with elevated ICP and normally elastic arteries, has a superficial resemblance to the shape of Z(t) described by Traczewski et al, for patients with normal ICP and inelastic arteries. But the cause of the shape of Z(t) is believed to be different in the two cases. In both cases, Z(t) is believed to reflect the changing arterial blood volume during a cardiac cycle. In FIG. 3B, the arteries are limited in how much they can expand immediately in response to the increase in blood pressure, because at elevated ICP the spinal cavity is less compliant and not as much CSF can flow into the spine to accommodate the increased volume of the arteries. The arteries continue to expand after the blood pressure inside the arteries reaches its maximum value at time 204, because the venous blood flows more quickly out of the head, reducing the pressure inside the cranium. In Traczewski et al, for the patients with inelastic arteries and normal ICP, the arteries are limited in how much they can expand immediately in response to the increase in blood pressure, because the walls of the arteries are not very elastic. The arteries continue to expand after the blood pressure inside the arteries reaches its maximum value, because the walls of the arteries continue to deform plastically, in response to the blood pressure, until the blood pressure drops below the ICP. Because elevated ICP and inelastic arteries have similar effects on the shape of Z(t), it is possible that using impedance to estimate CPP will not work as well in patients with poor artery elasticity.

The peak to peak Z(t), or a similar measure of the range of Z(t), may also be a useful indicator of ICP and/or CBV. The inventors have found evidence of this in tests, to be described below, in which ICP and CBV are both raised or both lowered, so it is not certain whether the effect is caused by ICP, or CBV, or both.

The rate of decrease in Z(t), which occurs around time 212 after the second peak in Z(t) in FIGS. 3A and 3B, may also provide information about ICP or CBV, since it tends to be proportional to the range of Z(t).

Another parameter of Z(t), which may provide a useful indicator of ICP, is the latency, or time delay, between the diastolic time 202, and a time 214 at which Z(t) is increasing at the maximum rate. The time delay is longer in FIG. 3A, for a subject with normal ICP, than it is in FIG. 3B, for a subject with elevated ICP. It is believed, based on test results and on a theoretical model, that this difference in Z(t) is associated with the difference in ICP in FIGS. 3A and 3B, rather than with the difference in CPP.

It should be understood that this indicator of ICP, as well as any of the other indicators proposed for intracranial parameters, may still be valid, even if the theoretical model is wrong.

According to the model, the delay between the diastolic time 202, and the time of maximum rate of increase of Z(t), is due to the time required for a pressure wave, associated with the contraction of the heart, to propagate to the cerebral arteries. When the heart begins to contract, some increase in pressure (and volume) in the cerebral arteries begins almost immediately, so the minimum of Z(t), which is believed to be primarily a measure of the volume of the large cerebral arteries, occurs at essentially the same time as the diastolic time of the heart beat. This is confirmed by ECG readings. However, there is a time delay in the bulk of the pressure rise, and hence the rise in Z(t), due to the compliance of the arteries leading from the heart to the brain, and particularly the cerebral arteries. This pressure wave propagates more quickly when the arteries are less compliant, and the cerebral arteries are less compliant when the ICP is elevated. Hence, it is expected that the time delay between the diastolic time 202, and the time 214 of maximum rate of increase in Z(t), will be shorter when ICP is elevated. Measuring this time delay in Z(t) can provide a direct estimate of ICP.

The impedance may be measured using any of a variety of known arrangements of electrodes for measuring bio-impedance. The configurations of electrodes and PPG sensors described in the published patent applications cited above may be particularly advantageous to use, because they may be relatively more sensitive to the blood volume in the brain and in large arteries in the head, and relatively less sensitive to the peripheral blood volume in the head, for example in the scalp. The use of separate voltage and current electrodes, in these and other configurations, has the potential advantage that the impedance measurement is relative less sensitive to the high impedance of the skin.

It is believed that the changes in Z(t) over a cardiac cycle in FIGS. 2A-3B may be most sensitive to the volume of blood in the larger arteries of the brain and head, because the pattern seen in Z(t) matches the pattern expected for changes in cerebral artery volume over a cardiac cycle. The changes in cerebral artery volume over a cardiac cycle are also known from direct measurements by imaging of the head, for example by ultrasound or MRI. The changes in impedance over a cardiac cycle may be relatively insensitive to the blood volume in the smaller cerebral arteries, and to the venous blood volume.

On the other hand, it is believed that the time-averaged impedance may depend significantly on the venous blood volume, as well as on the volume of blood that has hemorrhaged into the interior of the cranium, because blood has a somewhat higher electrical conductivity than CSF and other fluids in the head.

FIG. 5 shows a flowchart 700 for finding one or more of the intracranial parameters, according to an exemplary embodiment of the invention. At 702, data is obtained on the impedance Z(t). The data may be generated in real time by measurements on a subject, or data from earlier measurements may be retrieved from a data storage medium. Optionally, Z(t) is adjusted using PPG data, at this stage or later in the procedure, in order to make Z(t) less sensitive to changes in peripheral blood volume in the head, for example using any of the methods described in WO 06/006143, WO 06/011128, US 2005/0054939 or WO 03/059164.

The phases of the cardiac cycle are identified in 704, for example the diastolic phase in each cardiac cycle is identified and assigned a phase of 0 degrees. The diastolic phase may be identified, for example, by looking for periodic minima in Z(t), at a periodicity within a normal range for the heart rate. Alternatively or additionally, ECG data, which optionally is taken from the subject, is used in identifying the phases of the cardiac cycle. The data points between one diastolic phase and the next may be assigned phases from 0 to 360 degrees, linear with time t, for example.

At 706, values of Z with the same phase, from different cardiac cycles, are optionally averaged together. Such averaging has the potential advantage that it may produce a shape of Z(t), for purposes of finding intracranial parameters, that is more characteristic of the subject than data from a particular cardiac cycle is likely to be. The number of cardiac cycles used to find the average is optionally much greater than 1, but not so great that the parameters are likely to change substantially during the time over which the average is taken. For example, the averaging time is between 10 and 30 seconds, or between 30 seconds and 1 minute, or between 1 and 2 minutes, or less than 10 seconds, or more than 2 minutes. Optionally, ballistic averaging is used, in which for each cardiac cycle, the ballistic average is found by taking an average, or a weighted average, of Z(t) for that cycle, and the ballistic average for the previous cycle. Optionally, before averaging over different cardiac cycles, unusual cardiac cycles, for which Z(t) behaves very differently than in most cycles, are removed, since the data for such cycles may suffer from errors in measurement.

Alternatively, the intracranial parameters are found by analyzing Z(t) for a single cardiac cycle at a time. Optionally, Z(t) is smoothed. The averaging over more than one cardiac cycle, and the smoothing, both have the potential advantage that they may eliminate outlying points in Z, due to noise or errors in measurement. Such outlying points, if not eliminated, may introduce large errors when the maximum and minimum values of Z, or the maximum or minimum rate of change of Z, are used in a calculation for estimating intracranial parameters.

At 708, a measure is found for the range of Z during a cardiac cycle. In addition to being a useful parameter in itself, the range of Z may be used for normalizing features of Z(t) to a characteristic height. The normalized magnitudes of changes in Z(t), or rates of change of Z(t), may be more useful for estimating intracranial parameters, than the absolute magnitudes, which may be more sensitive to details of the size, shape and placement of the electrodes, for example. The maximum impedance $Z_{max}$ and the minimum impedance $Z_{min}$ are found, for example, and their difference $Z_{max}-Z_{min}$ is used as the measure. Alternatively, other measures are used for the range of Z during a cardiac cycle, for example the standard deviation in Z, or other functions of the distribution of values of Z. These other measures of the range of Z may be less sensitive to noise or errors than $Z_{max}-Z_{min}$, particularly if Z is not averaged over several cardiac cycles as described above.

The rest of flowchart 700 shows different methods of estimating intracranial parameters, all making use of the Z(t) data found in 704 or 706, and the measure of the range of Z(t) found in 708, done in parallel. All of the methods need not be used, and other methods may be used as well. If more than one method is used, they need not be done in parallel, but results of one method may be used to improve the accuracy of another method. For example, if the results of one method give abnormal results, this may indicate faulty attachment of the electrodes, or another error in the procedure, which should be corrected before analyzing the data according to another method. As another example, some adjustable parameters used in one of the methods, for example coefficients correlating a feature of Z(t) with one of the intracranial parameters, may have optimal values that differ for different ranges of the intracranial parameters, and the results of another method may help in choosing the optimal values of the free parameter to use in that method.

The first method uses the relative heights of the first and second peaks in Z(t), seen in FIGS. 3A and 3B, to evaluate CPP. The first method begins at 710, when $Z_1$, a first peak in Z(t) after $Z_{min}$, is found. The difference $Z_1-Z_{min}$ is then found. As noted above in the description of FIGS. 3A and 3B, $Z_1-Z_{min}$ is believed to be a useful indicator of CPP. Optionally, a first peak in Z is only accepted as $Z_1$ if it occurs approximately at the systolic phase of the cardiac cycle. Optionally, instead of a first local maximum in Z, $Z_1$ is defined as a first local minimum in the rate of rise dZ/dt, i.e. an inflection point in Z, after $Z_{min}$ and before $Z_{max}$, or $Z_1$ is defined as the first local maximum in Z or the first local minimum in dZ/dt, whichever comes first. Optionally, local minima in dZ/dt are only counted if they are sufficiently deep by some criterion, which has the potential advantage that the value of $Z_1$ may be more robust, and not very affected by noise. For example, a local minimum in dZ/dt is only counted if it is at least 20% less than the local maxima in dZ/dt on each side of it, or at least 50% less, or at least a factor of 2 less, or at least a factor of 5 less. Optionally, Z(t) is smoothed, to reduce noise, before applying the definition of $Z_1$, which may be advantageous because higher derivatives of Z(t) are likely to be more affected by noise than Z(t). Optionally, if there is no local maximum in Z, or no local minimum in dZ/dt that meets the criterion, between $Z_{min}$ and the absolute maximum $Z_{max}$, then $Z_1$ is set equal to $Z_{max}$, because this circumstance indicates that the first peak in Z(t) after $Z_{min}$ is $Z_{max}$.

At 712, $Z_1-Z_{min}$ is optionally normalized, for example by dividing it by the range of Z found at 708, since the normalized $Z_1-Z_{min}$ may be more indicative of CPP than the absolute $Z_1-Z_{min}$, which may be more sensitive to how the impedance is measured. Optionally, $Z_1-Z_{min}$ is normalized by dividing it by $Z_2-Z_{min}$, where $Z_2$ is the second local maximum in Z, even if $Z_2$ is less than $Z_1$. Optionally, $Z_2$ is the first point after $Z_1$ which is either a local maximum, or a local minimum in the absolute value of dZ/dt. The last case includes inflection points in the falling part of Z(t), after the absolute maximum. Although we refer below to the normalized $Z_1-Z_{min}$, the absolute $Z_1-Z_{min}$ may be used instead. This is also true for the normalized quantities found using the other methods described below.

A second method of estimating CPP begins at 714, with a determination of a rate of rise of Z(t). Optionally, the maximum rate of rise dZ/dt is used. Alternatively, another measure of the maximum rate of rise is used, for example the maximum rate of rise excluding outlying points, or the cardiac period is divided into intervals, and the maximum average rate of rise for any of the intervals is found. Optionally, only a portion of the cardiac period is considered when finding the measure of the maximum rate of rise, for example only the portion between the diastolic time and the first peak in Z(t). These alternative measures for rate of rise may be less sensitive to noise or errors in measurement than the maximum rate of rise. Optionally, at 716, the rate of rise is normalized, to the range of Z found at 708, to the cardiac period, or to both.

At 718, an estimate of CPP is made, from the normalized quantities found at 712, or 716, or both. Optionally, a separate estimate of CPP is made from each normalized quantity.

Optionally, if both normalized quantities are found, they are combined, for example by taking a weighted average, to obtain a single estimate of CPP. Optionally, the estimate of CPP is an absolute one. Alternatively or additionally, the normalized quantities are used to estimate a change in CPP relative to a baseline, using impedance data obtained from the same subject at an earlier time.

The estimate, or each estimate, of CPP made at 718 is based on an expected correspondence or at least a correlation between the normalized quantities and CPP. (As will be described below, this is also true of estimates made of the other intracranial parameters.) The correspondence may be determined by an experiment study, measuring $Z(t)$ in a variety of subjects, and measuring or estimating CPP in the same subjects using a different method, for example with a conventional invasive probe. A best fit is then optionally made between the normalized quantity or quantities and CPP, using this experimental data. Optionally, the experimental study is done with subjects differing in age, sex, weight, and/or other personal characteristics, and the best fit made separately depending on the values of these characteristics. The fit may be a linear fit, for example, matching the CPP to a linear function of the normalized quantity, or a nonlinear fit may be made, matching the CPP to any of a variety of nonlinear functions of the normalized quantities, using one or more free parameters. The function is used, at 718, to convert the normalized quantities to the estimate of CPP.

At 720, the estimate or estimates of CPP are optionally smoothed over a period of time. The period of time is, for example, much longer than a cardiac period, but not so long that the CPP is likely to change very much during the period of time. Any of the time periods mentioned above, for averaging $Z(t)$ over different cardiac cycles, may be used for smoothing CPP over time. The smoothed CPP may provide a more accurate value of CPP than the unsmoothed estimate.

A method of estimating ICP begins at 722. A latency time is found, between the diastolic time and a characteristic time of the maximum rate of increase $dZ/dt$. Optionally, the diastolic time is defined as the time that $Z(t)$ is at a minimum. Alternatively, the diastolic time is defined from ECG data, taken from the subject when $Z(t)$ is measured, or any other known method is used to determine the diastolic time, or a combination of methods is used.

The characteristic time of the maximum rate of increase may be the actual time when the measured $dZ/dt$ is at a maximum value during a cardiac cycle. Alternatively, various other methods may also be used for defining a characteristic time of the maximum rate of increase, similarly to the way that various methods can be used to define a characteristic maximum rate of increase of $Z(t)$, as described above. These other methods may make the characteristic time less sensitive to noise or errors in measurement. For example, outlying points in $dZ/dt$ may be eliminated before finding the maximum $dZ/dt$, or only the average $dZ/dt$ over chosen intervals may be considered when finding the maximum $dZ/dt$, and the characteristic time may be defined as the center of the interval with the maximum average $dZ/dt$.

Optionally, when using this method, a check is made to see that the diastolic time as indicated by ECG data is very close to the minimum in $Z(t)$. If this is not true, then it may mean that the impedance data is dominated by the blood volume of veins, rather than arteries, and that the estimates of ICP obtained using this method may not be very accurate. Such a situation might occur, for example, if the electrodes used for the impedance measurement are not placed properly. It might also occur in certain subjects, due to differing physiology.

At 724, the latency time found at 722 is optionally normalized to the cardiac period, and at 726, the normalized latency period is used to find an estimate of ICP, using any of the methods described above for finding an estimate of CPP at 718. The inventors have found that the time from diastole to systole may vary less, at different times and between different subjects, than the cardiac period, so the unnormalized latency period may provide a more reliable estimate of ICP than the normalized latency period. The estimate of ICP is optionally smoothed at 728, similarly to the smoothing of the estimate of CPP at 720.

A method of estimating ICP or CBV begins at 730. A characteristic greatest rate of fall in $Z(t)$ is found. The greatest rate of fall in impedance is often observed to occur after the second peak in $Z(t)$ after the diastolic phase, and optionally only a time interval following the second peak is considered, when finding the greatest rate of fall. Alternatively, an average rate of fall during a time interval following the second peak is used, instead of a maximum rate of fall, which has the potential advantage that it may be less sensitive to noise. At 732, the rate of fall found at 730 is optionally normalized, by dividing it by the range of $Z$ found at 708. Optionally, the rate of fall is also normalized by dividing it by the heart rate, i.e. multiplying it by the cardiac period.

At 734, an estimate of ICP or CBV is made from the normalized rate of fall found at 732. Optionally, the range of $Z$ found at 708, or a different measure of the range of $Z$, is also used to estimate ICP or CBV, since tests indicate that the range of $Z$ is also a useful indicator of ICP or CBV. Optionally, only a single estimate of ICP or CBV is made, based both on the rate of fall and on the range of $Z$. Alternatively, two separate estimates of ICP and/or CBV are made. Optionally, only the range of $Z$ is used at 734 to estimate ICP or CBV, and the rate of fall is not used. Optionally, $Z(t)$ time-averaged over one or more cardiac cycles is used to estimate CBV at 734, together with, in addition to, or instead of, using the range of $Z$, and/or the rate of fall of $Z$, to estimate CBV. Any of the methods described above, for making an estimate of CPP at 718, may be used for making an estimate or estimates of ICP or CBV at 734, starting with the normalized rate of fall of $Z(t)$ and/or the range of $Z$, instead of the normalized quantities found at 712 and 716. The estimate or estimates of ICP and/or CBV are optionally smoothed at 736, using any of the methods described for smoothing the estimate of CPP at 720.

At 738, integrated values for the intracranial parameters are optionally found, based on the optionally smoothed values found at 720, 728, and 736. Optionally, if more than one estimate was made of any of the parameters, then the estimates are combined into a single estimate of that parameter, for example by taking a weighted average. If two estimates of the same parameter are very different from each other, then a warning is optionally given that a combined estimate may be unreliable, and that the impedance measuring apparatus may have a problem that needs correcting. Optionally, if one estimate of an intracranial parameter is further from an expected value, based on experience with other patients with similar clinical indications, then that method is given less weight. This option may be implemented as part of an automatic calculation, using data from clinical studies to choose an algorithm, or it may be implemented manually, with a physician assigning weights based on his judgment.

Optionally, the values of one or more parameters are used to improve the estimates of one or more other parameters. For example, the fitting function used to find CPP from the normalized quantities found at 712 and 716, described above, may itself depend on the value of ICP and/or CBV, and the estimates found for these parameters at 726 and 734 may be used to find an improved estimate of CPP. Since this may also be true of parameters other than CPP, the procedure is optionally iterative, and optionally continues until values for all of the intracranial parameters converge.

Optionally, values of the intracranial parameters are checked for consistency with other data about the subject, and are corrected, or a warning is given, if an inconsistency is found. For example, the CIAP, which is the sum of the ICP and the CPP, is normally expected to be no greater than the central MAP (adjusted for the height of the subject's head relative to the chest), which may be measured by any standard blood pressure sensor.

peak, also expected to be positively correlated with CPP; and 4) the latency time between the diastolic time, indicated by the minimum in $Z(t)$, and the time of maximum $dZ/dt$, not normalized to the cardiac period, which is expected to be negatively correlated with ICP.

Table 1 lists the mean value and standard deviation for the baseline value (averaged between the before and after baseline measurements), and for the perturbed value, for each of the four indicators, for each of the two tests. Using the before baseline value, or the after baseline value, instead of the average baseline value, would not change any of the results very much.

TABLE 1

Test Results

| Test | Indicator | Baseline value | | Perturbed value | | Change from baseline value | |
| --- | --- | --- | --- | --- | --- | --- | --- |
| | | mean | s.d. | mean | s.d. | mean | s.d. |
| Head down | Peak-to-peak | 3820 | 1690 | 6450 | 2270 | +2630 | 1370 |
| | Normalized max. dZ/dt | 17.72 | 2.35 | 11.28 | 2.86 | −6.44 | 3.22 |
| | Height of 1$^{st}$ peak | 95.1 | 8.2 | 65.0 | 12.0 | −30.1 | 15.8 |
| | Latency time | 0.0395 | 0.0041 | 0.0368 | 0.0028 | −0.0027 | 0.0033 |
| Endarterectomy | Peak-to-peak | 6220 | 2480 | 4590 | 2110 | −1640 | 820 |
| | Normalized max. dZ/dt | 13.82 | 4.04 | 9.62 | 1.60 | −4.20 | 3.38 |
| | Height of 1$^{st}$ peak | 76.4 | 11.1 | 62.9 | 7.9 | −13.5 | 11.9 |
| | Latency time | 0.0547 | 0.0141 | 0.0877 | 0.0429 | +0.0330 | 0.0393 |

Table 1 shows the mean values and standard deviations for four indicators of intracranial parameters, in two tests in which the intracranial parameters were perturbed. The first test is referred to as "head down" in Table 1. In this test, done with healthy subjects, the subject rested on his back on a flat surface, with his head raised above his chest, while a baseline measurement of $Z(t)$ was made. His head was then lowered below the level of his chest, while another measurement of $Z(t)$ was made. Finally, his head was raised again to its initial position, and a second baseline measurement of $Z(t)$ was made. It is expected that lowering the head below the level of the chest will cause an increase in ICP, and in CBV, because venous blood pools in the head. It is also expected to cause a decrease in CPP, because the increase in ICP should be greater than any increase in CIAP that may occur.

The second test is referred to as "endarterectomy" in Table 1. This test was done on patients undergoing an endarterectomy procedure, in which the carotid artery on one side of the neck is temporarily clamped. Baseline measurements of $Z(t)$ are made before and after the clamping, and a measurement of $Z(t)$ is made during the time the carotid is clamped. It is expected that, during the time the carotid is clamped, ICP and CBV will decrease, because venous blood will drain out of the head faster than blood is supplied by the remaining unclamped arteries. CPP is also expected to decrease, due to the decrease in CIAP caused by the clamping of the carotid.

The four indicators measured during these tests were 1) peak-to-peak $Z(t)$ in arbitrary units, believed to be positively correlated with CBV; 2) normalized maximum $dZ/dt$, expected to be positively correlated with CPP; 3) the height of the first peak in $Z(t)$, normalized to the height of the highest All four indicators changed in the direction expected in both tests. Because the sample size was 15 or 16, the statistical uncertainty in the mean values of the indicators is about one quarter of the standard deviation, so the difference between the baseline value and the perturbed value is several times greater than the statistical uncertainty in the values in all cases, and the results are very statistically significant.

In the case of the peak-to-peak indicator, the standard deviation of the change is substantially less than the standard deviation of the baseline and perturbed values, for both tests. This may indicate that the peak-to-peak indicator is particularly sensitive for detecting changes in intracranial parameters in a given subject.

In the case of the height of the first peak in $Z(t)$, the change during the head down test was several times greater than the standard deviation for both the baseline and perturbed values, suggesting that the height of the first peak is likely to be a useful indicator for determining intracranial parameters, both absolutely and relative to earlier times. This is also true for the maximum $dZ/dt$ indicator during the head down test.

The change in latency time was a few times greater than the standard deviation in baseline values for the endarterectomy test, suggesting that this indicator is also likely to be useful for measuring intracranial parameters. The standard deviation for the perturbed value is greater than for the baseline values, in the endarterectomy test, but this is likely due to different clinical conditions for the different subjects when the carotid was clamped, rather than being due to any intrinsic errors in the accuracy of the indicator.

The changes in the maximum $dZ/dt$ indicator and the "height of the first peak" indicator were comparable to the corresponding standard deviations in the baseline values, for the endarterectomy test, which may suggest that these indicators would be most useful for detecting somewhat greater changes in the intracranial parameters than occurred in the endarterectomy test, for most patients. Further evidence for this suggestion may be seen for one patient, who had greater changes in these indicators than any of the other patients, out of a sample of 16 patients. That patient was the only one to show symptoms of neurological damage, during the time the carotid was clamped, suggesting that indeed he had a greater decrease in CPP than any of the other patients.

A combination of two or more indicators may be even more useful, for detecting changes in intracranial parameters, than any single indicator. For example, FIG. 6 shows a graph 300 of the distribution of a combined indicator for CPP, for the sample of 16 patients in the endarterectomy test. The combined indicator consists of the sum of the perturbed value of the normalized maximum dZ/dt, the percentage change in the normalized maximum dZ/dt from its baseline value for that patient, the perturbed value of the indicator based on the height of the first peak in Z(t), and the percentage change in that indicator from its baseline value. A lower value of the combined indicator, corresponding to the left side of the x-axis, indicates a lower CPP when the carotid was clamped. Note that there is a single patient in the most negative bin 302 of the range of the combined indicator. This was the one patient who exhibited neurological symptoms during the clamping of the carotid.

As used herein, "estimating" a cerebral hemodynamic parameter includes estimating changes in the value of the parameter from a baseline, as well as estimating the value of the parameter absolutely. This is also true of "measuring," "determining," and similar words.

The invention has been described in the context of the best mode for carrying it out. It should be understood that not all features shown in the drawings or described in the associated text may be present in an actual device, in accordance with some embodiments of the invention. Furthermore, variations on the method and apparatus shown are included within the scope of the invention, which is limited only by the claims. Also, features of one embodiment may be provided in conjunction with features of a different embodiment of the invention. As used herein, the terms "have", "include" and "comprise" or their conjugates mean "including but not limited to."

The invention claimed is:

1. A cranial diagnostic apparatus comprising:
   at least one processor configured to:
   receive impedance data indicative of electrical impedance measured via a subject's head;
   correlate the impedance data with a timing of at least a portion of a cardiac cycle;
   identify in the data a first impedance characteristic correlated to the portion of the cardiac cycle;
   identify in the data a second impedance characteristic correlated to the portion of the cardiac cycle;
   compare the first impedance characteristic with the second impedance characteristic; and
   estimate at least one intracranial hemodynamic parameter from the comparison of the first and the second impedance characteristics.

2. The apparatus of claim 1, wherein the hemodynamic parameter includes at least one of intracranial pressure, cerebral perfusion pressure, cerebral blood volume, and a mean transit time through cerebral capillaries.

3. The apparatus of claim 2, wherein the first impedance characteristic is reflective of a first local maximum impedance and wherein the second impedance characteristic is reflective of a second local maximum impedance.

4. The apparatus of claim 2, wherein the first impedance characteristic is reflective of a maximum rate of rise in impedance.

5. The apparatus of claim 2, wherein the first impedance characteristic is reflective of a maximum rate of fall in impedance.

6. The apparatus of claim 2, wherein the first impedance characteristic is reflective of a range of impedance between a minimum and a maximum.

7. The apparatus of claim 1, wherein the hemodynamic parameter includes intracranial pressure.

8. The apparatus of claim 1, wherein the at least one processor is further configured to remove variations in the data due to the subject's breathing cycle.

9. The apparatus of claim 1, wherein the first impedance characteristic is reflective of a local maximum impedance.

10. The apparatus of claim 1, wherein the first impedance characteristic is reflective of a local minimum in rate of rise of impedance.

11. The apparatus of claim 1, wherein the first impedance characteristic is reflective of a maximum rate of rise of impedance and wherein the second impedance characteristic is reflective of a local maximum in impedance.

12. The apparatus of claim 1, wherein the first impedance characteristic is reflective of a maximum rate of rise of impedance and wherein the second impedance characteristic is reflective of a local minimum in rate of rise of impedance.

13. The apparatus of claim 1, wherein the at least one processor is further configured to normalize the data to a total range of impedance between a minimum and a maximum.

14. The apparatus of claim 1, wherein the first impedance characteristic is reflective of a latency time.

15. The apparatus of claim 1, wherein the at least one processor is further configured to average the estimate of the at least one intracranial hemodynamic parameter over a plurality of cardiac cycles.

16. The apparatus of claim 1, wherein identifying a first impedance characteristic includes averaging the data from a same phase of a plurality of cardiac cycles and wherein identifying a second impedance characteristic includes averaging the data from a same phase of a plurality of cardiac cycles.

17. The apparatus of claim 1, wherein the at least one processor is further configured to monitor the at least one intracranial hemodynamic parameter substantially continuously for a subject for a period of time.

18. The apparatus of claim 1, wherein the at least one processor is further configured to receive data indicative of the subject's blood pressure.

* * * * *